US011291660B2

(12) United States Patent
Kaye

(10) Patent No.: US 11,291,660 B2
(45) Date of Patent: *Apr. 5, 2022

(54) METHOD OF TREATING HEART FAILURE WITH PRESERVED EJECTION FRACTION BY ADMINISTERING MILRINONE

(71) Applicant: Baker Heart and Diabetes Institute, Melbourne (AU)

(72) Inventor: David Kaye, Beaumaris (AU)

(73) Assignee: Baker Heart and Diabetes Institute, Melbourne (AU)

( * ) Notice: Subject to any disclaimer, the term of this patent is extended or adjusted under 35 U.S.C. 154(b) by 0 days.

This patent is subject to a terminal disclaimer.

(21) Appl. No.: 16/700,237

(22) Filed: Dec. 2, 2019

(65) Prior Publication Data

US 2020/0101053 A1    Apr. 2, 2020

Related U.S. Application Data

(63) Continuation of application No. 15/538,123, filed as application No. PCT/AU2015/050820 on Dec. 21, 2015, now Pat. No. 10,493,067.

(30) Foreign Application Priority Data

Dec. 22, 2014  (AU) ................................ 2014905194

(51) Int. Cl.
| | |
|---|---|
| A61K 31/444 | (2006.01) |
| A61K 9/20 | (2006.01) |
| A61K 9/28 | (2006.01) |
| A61K 9/48 | (2006.01) |
| A61K 9/50 | (2006.01) |

(52) U.S. Cl.
CPC ............ *A61K 31/444* (2013.01); *A61K 9/205* (2013.01); *A61K 9/2018* (2013.01); *A61K 9/2054* (2013.01); *A61K 9/2846* (2013.01); *A61K 9/2853* (2013.01); *A61K 9/2866* (2013.01); *A61K 9/2886* (2013.01); *A61K 9/4808* (2013.01); *A61K 9/5026* (2013.01); *A61K 9/5078* (2013.01)

(58) Field of Classification Search
CPC .... A61K 31/444; A61K 9/2018; A61K 9/205; A61K 9/2054; A61K 9/2846; A61K 9/2853; A61K 9/2866; A61K 9/2886; A61K 9/4808; A61K 9/5026; A61K 9/5078

See application file for complete search history.

(56) References Cited

U.S. PATENT DOCUMENTS

| | | | | | |
|---|---|---|---|---|---|
| 4,312,875 | A | ‡ | 1/1982 | Lesher | C07D 213/61 514/33 |
| 4,313,951 | A | ‡ | 2/1982 | Lesher | C07D 213/50 514/33 |
| 4,806,361 | A | ‡ | 2/1989 | Harrison | A61K 9/5078 424/49 |
| 4,871,548 | A | ‡ | 10/1989 | Edgren | A61K 9/2086 424/48 |
| 5,009,895 | A | ‡ | 4/1991 | Lui | A61K 9/2054 424/46 |
| 5,213,811 | A | ‡ | 5/1993 | Frisbee | A61K 9/5078 424/45 |
| 5,681,582 | A | ‡ | 10/1997 | Gilis | A61K 9/209 424/46 |
| 10,493,067 | B2 | * | 12/2019 | Kaye | A61K 9/2018 |
| 2004/0081693 | A1 | ‡ | 4/2004 | Woo | A61K 9/205 424/46 |
| 2005/0095292 | A1 | ‡ | 5/2005 | Benjamin | A61K 9/2866 424/46 |
| 2009/0220611 | A1 | ‡ | 9/2009 | Dargelas | A61K 9/2077 424/49 |
| 2011/0268799 | A1 | ‡ | 11/2011 | Dixit | A61K 9/209 424/46 |
| 2015/0018353 | A1 | ‡ | 1/2015 | Kim | C07D 413/14 514/23 |
| 2017/0348292 | A1 | * | 12/2017 | Kaye | A61K 31/444 |

FOREIGN PATENT DOCUMENTS

| | | | |
|---|---|---|---|
| EP | 0 164 959 A2 | ‡ | 12/1985 |
| GB | 2 065 642 B | ‡ | 7/1981 |
| JP | 61-001614 A | ‡ | 1/1986 |
| JP | 7-053364 A | ‡ | 2/1995 |
| JP | 9-509412 A | ‡ | 9/1997 |
| JP | 10-507210 A | ‡ | 7/1998 |
| JP | 2004-143175 A | ‡ | 5/2004 |
| JP | 2005-537298 A | ‡ | 12/2005 |
| WO | WO 1995/020946 A1 | ‡ | 8/1995 |

(Continued)

OTHER PUBLICATIONS

Edelmann et al., "Effect of spironolactone of diastolic function and exercise capacity in patients with hear failure with preserved ejection fraction", 2013, JAMA, vol. 309(8), pp. 781-791.‡
Edelson et al., "High-performance liquid chromatographic analysis of milrinone in plasma and urine: Intravenous pharmacokinetics in the dog", 1983, Journal of Chromatography, 276, pp. 456-462.‡
Foody et al., "p-blocker therapy in heart failure", 2002; JAMA, vol. 287(7), pp. 883-889.‡
Givertz et al., "Effect of Bolus Milrinone on Hemodynamic Variables and Pulmonary Vascular Resistance in Patients with Severe Left Ventricular Dysfunction: a Rapid Test for Reversibility of Pulmonary Hypertension," JAm ColiCardiol, vol. 28(7), pp. 1775-1780 (1996).‡
Goldstein et al., "Electrophysiologic Effects of Milrinone in Patients with Congestive Heart Failure," AmjCardiol, vol. 57(8), pp. 624-628 (1986).‡

(Continued)

*Primary Examiner* — Mina Haghighatian
*Assistant Examiner* — Nathan W Schlientz
(74) *Attorney, Agent, or Firm* — Knobbe, Martens, Olson & Bear, LLP

(57) ABSTRACT

The present invention relates to methods of treating subjects having heart failure with preserved ejection fraction (HFpEF) with a sustained-delivery formulation of cardiotonic 5-(pyridinyl)-2(1H)-pyridinone compounds.

24 Claims, No Drawings

(56) References Cited

FOREIGN PATENT DOCUMENTS

| WO | WO 1997/016172 A1 | ‡ | 5/1997 | | |
|---|---|---|---|---|---|
| WO | WO 2004/012715 A1 | | 2/2004 | | |
| WO | WO 2010/133815 A1 | | 11/2010 | | |
| WO | WO 2013/023250 | ‡ | 2/2013 | ......... | A61K 2300/00 |
| WO | WO 2013/023250 A1 | | 2/2013 | | |
| WO | WO 2013/116194 A2 | | 8/2013 | | |

OTHER PUBLICATIONS

Cusick et al., "Effects of Intravenous Milrinone Followed by Titration of High-does Oral Vasodilator Therapy on Clinical Outcome and Rehospitalization Rates in Patients with Severe Heart Failure," American Journal of Cardiology, vol. 82(9), pp. 1060-1065 (1998).‡

Das et al., "Disposition of Milrinone in Patients After Cardiac Surgery," British Journal of Anaesthesia, vol. 72(4), pp. 426-429 (1994).‡

De Hert et al., "Comparison of Two Different Loading Doses of Milrinone for Weaning from Cardiopulmonary Bypass," Journal of Cardiothoracic and Vascular Anesthesia, vol. 9(3), pp. 264-271 (1995).‡

Doolan et al., "A Placebo-controlled Trial Verifying the Efficacy of Milrinone in Weaning High-risk Patients from Cardiopulmonary Bypass," Journal of Cardiothoracic and Vascular Anesthesia, vol. 11(1), pp. 37-41 (1997).‡

Gorodeski, et al., "Prognosis on chronic dobutamine or milrinone infusions for stage D heart failure," Circ Heart Fail., vol. 2. p. 320, Originally published online May 14, 2009, 9 pages.‡

Hasking et al., "Effect of autonomic blockade on the hemodynamic responses of normal human subjects to acute intravenous milrinone," Journal of Cardiovascular Pharmacology (1987), 9(5), 515-18.‡

Hatzizacharias, et al., "Intermittent milrinone effect on long-term hemodynamic profile in patients with severe congestive heart failure," American Heart Journal (1999), 138(2 Pt. 1), 241-246.‡

Hayashida, et al. "Inhibitory effect of milrinone on cytokine production after cardiopulmonary bypass," The Annas of Thoracic Surgery, vol. 68, No. 5, 1661-1667(1999).‡

Butterworth et al., "A Pharmacokinetic and Parmacodynamic Evaluation of Milrinone in Adults Undergoing Cardiac Surgery," Anesthesia * Analgesia, vol. 81, No. 4, pp. 783-792 (1995).‡

Canver et al., "Milrinone for Long-term Pharmacologic Support of the Status 1 Heart Transplant Candidates," The annals of Thoracic Surgery, vol. 69, No. 6, pp. 1823-1826 (2002).‡

Cesario et al., "Beneficial Effects of Intermittent Home Administration of the Inotrope/Vasodllator Milrinone in Patients with Endstate Congestive Heart Failure: a Preliminary Study," American Heart Journal, vol. 135(1), pp. 121-129 (1998).‡

Chang et al., "Milrinone: Systemic and Pulmonary Hemodynamic Effects in Neonates After Cardiac Surgery," Critical Care Medicine, vol. 23(11), pp. 1907-1914(1995).‡

Clark et al., "Uncovering a Hidden Epidemic: a Study of the Current Burden of Heart Failure in Australia," Heart Lung Circ, vol. 13, pp. 266-273 (2004).‡

Alousi et al., "Pharmacology of the bipyridines: Amrinone and Milrinone," Circulation, vol. 73(3 Pt 2), 11110-11124 (1986).‡

Colucci, W.S., "Cardiovascular Effects of Milrinone," American Heart Journal, vol. 121 (6 Pt 2), pp. 1945-1947 (1991).‡

Amsallem et al., Phosphodiesterase III inhibitors for heart failure (review), 2005, Cochrane Database of Systematic Reviews, 1, pp. 2 and 6.‡

Colucci et al., "Efficacy of phosphodiesterase inhibition with milrinone in combination with converting enzyme inhibitors in patients with heart failure", 1993, JACC, vol. 22(4), pp. 113A-118A.‡

Arakawa et al., "Milrinone for the Treatment of Cerebral Vasospasm After Subarachnoid Hemorrhage: Report of Seven Cases," Neurosurgery, vol. 48(4), pp. 723-728 (2001).‡

Copp et al., "Overview of the Effects of Intravenous Milrinone in Acute Heart Failure Following Surgery," European Journal of Anaesthesiology, Supplement, vol. 5, pp. 35-41 (1992).‡

Bailey et al., "The Pharmacokinetics of Milrinone in Pediatric Patients After Cardiac Surgery," Anesthesiology, vol. 90(4), pp. 1012-1018 (Apr. 1999).‡

Baim et al., "Evaluation of a New Bipyridine Inotropic Agent-Milrinone-in Patients with Severe Congestive Heart Failure," The New England Journal of Medicine, vol. 309(13), pp. 748-756 (1983).‡

Abraham et al. (2005) In-hospital mortality in patients with acute decompensated heart failure requiring intravenous vasoactive medications. An analysis from the acute decompensated heart failure national registry (ADHERE). Journal of the American College of Cardiology 2005;46(1):57-64.‡

Acharya et al. (2016) Infections, arrhythmias, and hospitalizations on home intravenous inotropic therapy. Am J Cardiol 2016; 117:952-956.‡

Al Kindi et al., "Sustained release of milrinone delivered via microparticles in a rodent model of myocardial infarction", 2014, Journal of Thorac Cardiovasc Surg, vol. 148, pp. 2316-2324.‡

Medical Device Development Tool (MDDT) Qualification Decision Summary for Kansas City Cardiomyopahy Questionnaire (KCCQ), MDDT020, Oct. 19, 2017.‡

Shah, et al. (2016) Phenotype-specific treatment of heart failure with preserved ejection fraction: a multiorgan roadmap. Circulation. 134:73-90.‡

Ponikowski, et al. (2016) ESC Guidelines for the diagnosis and treatment of acute and chronic heart failure. European Heart Journal. 85 pages.‡

De Boer, et al. (2018) Association of cardiovascular biomarkers with incident heart failure with preserved and reduced ejection fraction. JAMA Cardiology. 3(3):215-224.‡

Maeder, et al. (2010) Hemodynamic basis of exercise limitation in patients with heart failure and normal ejection fraction. Journal of the American College of Cardiology. 56(11):855-863.‡

Borlaug, B.A. (2014) The pathophysiology of heart failure with preserved ejection fraction. Nature Reviews Cardiology. 11:507-515.‡

Oktay, et al. "The emerging epidemic of heart failure with preserved ejection fraction" Curr. Heart Fail. Rep. Dec. 2013, 10(4):1-17.‡

Paulus, et al. "A novel paradigm for heart failure with preserved ejection fraction" Journal of the American College of Cardiology. 2013:62(4):263-271.‡

Butler, et al. "Developing therapies for heart failure with preserved ejection fraction: current state and future directions" JACC Heart Fail. Apr. 2014, 2(2):97-112.‡

Monrad, et al. "Improvement in indexes of diastolic performance in patients with congestive heart failure treated with milrinone" Circulation 70.6 (1984): 1030-1037.‡

Braunwald's Heart Disease: A textbook of Cardiovascular Medicine, 10th ed. Philadelphia, PA: Elsevier Saunders (2015), p. 1562.‡

Sanderson "HFNEF, HFpEF, HF-PEF, or DHF What is in an Acronym?" JACC: Heart Failure (2014) 2(1):93-94.‡

Reddy et al. "A Simple, Evidence-Based Approach to Help Guide Diagnosis of Heart Failure with Preserved Ejection Fraction" Circulation (2018) 138:861-870 & Supplemental material in 19 pgs.‡

Shah. "Heart Failure with Preserved Ejection Fraction: A Clinician's Perspective" ASE State of the Art 2016. 96 pgs.‡

Shah et al. "Phenotypic Spectrum of Heart Failure with Preserved Ejection Fraction" Heart Fail Clin. (2014) 10(3):408-418.‡

Luo et al. "Clinical observation on Milrinone Treatment to Advanced Age Diastolic Heart Failure" Chinese Journal of Current Clinical Medicine (2011) 9(3):148-150.‡

Chinese Heart Failure Guidelines "Guidelines for the Diagnosis and Treatment of Chronic Heart Failure" Chin J Cardiol. (2007) 35(12):1076-1095.‡

Borlaug et al. "Heart Failure with Preserved Ejection Fraction: Pathophysiology, Diagnosis, and Treatment" European Heart Journal (2011) 32 670-679.‡

Xuesheng Luo, Shanshan Wang, Sui Chen, Lin Chen, Qi Li, and Jian Zhang, "Clinical Observation on Milrinone Treatment to Aged

(56) References Cited

OTHER PUBLICATIONS

Diastolic Heart Failure", Chinese Journal of Current Clinical Medicine, 2011, 9(3), 148-150, Abstract only. (Year: 2011).‡

Marjan Mujib, etc., "Angiotensin-converting Enzyme Inhibitors and Outcomes in Heart Failure and Preserved Ejection Fraction", The American Journal of Medicine, 2013, 126(5), 401-410. (Year: 2013).‡

Shannan K. Hamlin, Penelope S. Villars, Joseph T. Kanusky, and Andrew D. Shaw, "Role of Diastole in Left Ventricular Function, II: Diagnosis and Treatment", American Journal of Critical Care, Nov. 2004, 13(6), 453-466. (Year: 2004).‡

Aisling J. Carroll, etc., "Restrictive Cardiomyopathy With Preserved Ejection Fraction: Outcomes of Inotropic Support", Journal of the American College of Cardiology, 2009, 53(10), Supp. S, A159. (Year: 2009).‡

Alousi et al., "Pharmacoloay of the bipyridines: Amrinone and Milrinone," *Circulation*, vol. 73(3 Pt 2), III10-III24(1986).

Cesario et al., "Beneficial Effects of Intermittent Home Administration of the Inotrope/Vasodilator Milrinone in Patients with End-state Congestive Heart Failure: a Preliminary Study," *American Heart Journal*, vol. 135(1), pp. 121-129 (1998).

Foody et al., "β-blocker therapy in heart failure", 2002; *JAMA*, vol. 287(7), pp. 883-889.

Givertz et al., "Effect of Bolus Milrinone on Hemodynamic Variables and Pulmonary Vascular Resistance in Patients with Severe Left Ventricular Dysfunction: a Rapid Test for Reversibility of Pulmonary Hypertension," *J Am CollCardiol*, vol. 28(7), pp. 1775-1780 (1996).

Masking et al., "Effect of autonomic blockade on the hemodynamic responses of normal human subjects to acute intravenous milrinone," *Journal of Cardiovascular Pharmacology* (1987), 9(5), 515-18.

He and Yang, "Inhibition of vasoconstriction by phosphodiestearase III inhibitor milrinone in human conduit arteries used as coronary bypass grafts," Journal of Cardiovascular Pharmacology, vol. 28, No. 2, pp. 208-214 (Aug. 1996), accessed from httg_://jou rnals.iww.corn/cardiovascu lar12 1arm/Fuiitexti1996/08000i Inhibition of Vas con . . . , Apr. 24, 2014, 8 pages.

Hobbs, et al., "Impact of heart failure and left ventricular systolic dysfunction on quality of life: a cross-sectional study comparing common chronic cardiac and medical disorders and a representative adult population," European Heart Journal, vol. 23, No. 23, pp. 1867-1876 (Dec. 2002).

Hoffman, et al., "Efficacy and safety of milrinone in preventing low cardiac output syndrome in infants and children after corrective surgery for congenital heart disease," Circulation, vol. 107, No. 7, pp. 996-1002 (Feb. 25, 2003), published online Feb. 10, 2013, 8 pages.

Juenger, et al., "Health related quality of life in patients with congestive heart failure: comparison with other chronic diseases and relation to functional variables," Heart, vol. 87, No. 3, pp. 235-241, (2002), 8 pages.

Kibria et al., "Effect of plasticizer on release kinetics of diclofenac sodium pellets coated with eudragit RS 30 D", 2008, *AAPS PharmSciTech*, vol. 9(4), pp. 1240-1246.

Kikura, et al., "The effect of milrinone on hemodynamics and left ventricular function after emergence from cardiopulmonary bypass," Anesthesia & Analgesia (Baltimore), vol. 85, No. 1, pp. 16-22 (1997).

Komajda et al., "Heart failure with preserved ejection fraction: a clinical dilemma", 2014, *European Heart Journal*, vol. 35(16), pp. 1022-1032.

Kumar, Dissolution, Remington, The Science of Practice and Pharmacy, 21$^{st}$ Edition, Lippincott Williams & Wilkins, pp. 672-680, 2006.

Leier, Carl V., "Positive inotropic therapy: an update an new agents" 1996, *Current problems in cardiology*, vol. 21 (8), pp. 545-547.

Lloyd-Jones, et al., "Executive Summary: Heart Disease and Stroke Statistics—2010 Update: A Report from the American Heart Association", Circulation, vol. 121, pp. 948-954, and e259, (2010), 9 pages.

Lobato et al., "Effects of milrinone versus epinephrine on grafted internal mannary artery flow after cardiopulmonary bypass," *Journal of Cardiothoracic and Vascular Anesthesia*, Feb. 2000, 14(1), 9-11.

Loffredo et al., "Heart failure with preserved ejection fraction: molecular pathways of the ageing myocardium", 2014, *Circ Res.*, vol. 115, pp. 97-107.

Marius-Nunez et al., "Intermittent inotropic therapy in an outpatient setting: a cost-effective therapeutic modality in patients with refractory heart failure," *American Heart Journal*, Oct. 1996, 132(4), 805-8.

McMurray et al., "Heart failure," *Lancet*, 365:1877-1889, May-Jun. 2005.

Marvin, M.H.. "Diseases of the Heart and Blood Vessels. Nomenclature and Criteria for Diagnosis," *Arch Intern Med*, vol. 113(6), pp. 906-907 (1964).

Mehra et al., "Safety and clinicalutility of long-term intravenous milrinone in advanced heart failure," *American Journal of Cardiology*, vol. 80(1), pp. 61-64, Jul. 1997.

Messer et al., "Patterns of human mycardial oxygen extraction during rest and exercise," *J. Clin. Invest.*, 1962, 41:725-742.

Metoprolol Succinate Extended-Release Tablets, NDA 19-962 /S-032, pp. 3-17, Rev. 03/06, appeared to be posted on FDA website https://www.accessdata.fda.gov/drugsatfda__docs/label/2006/019962s032lbl.pdf in May 2008 see https://www.accessdata.fda.gov/drugsatfda_docs/nda/2006/021956s000TOC.cfm.

Milfred-Laforest et al., "Tolerability of extended duration intravenous milrinone in patients hospitalized for advanced heart failure and the usefulness of uptitration of oral angiotensin-converting enzyme inhibitors," *American Journal of Cardiology*, 1999, vol. 84(8), pp. 894-899.

Monrad, et al., "Improvement in indexes of diastolic performance in patients with congestive heart failure treated with milrinone," Circulation, vol. 70, No. 6, pp. 1030-1037 (Dec. 1984).

Monrad, et al., "Effects of milrinone on coronary hemodynamics and myocardial energetics in patients with conaestive heart failure," Circulation, vol. 71, No. 5, pp. 972-979 (May 1985).

Nichols, Principles and Practice of Therapeutic Drub Monitoring, slides of James H. Nichols, Professor of Pathology, Microbiology and Immunology, Medical Director, Clinical Chemistry, Associate Medical Director of Clinical Operations, Vanderbilt University School of Medicine, Nashville, TN not dated, 39 slides.

Package insert tor Sanofi-Aventis U.S. LLC's PRIMACOR® (Milrinone Lactate Injection) product, dated 2007.

Packer et al., "Effect of oral milrinone on mortality in sever chronic heart failure" *The New England Journal of Medicine*, 1991, vol. 325(21), pp. 1468-1475.

Pamboukian et al., The use of milrinone in pre-transplant assessment of patients with congestive heart failure and pulmonary hypertension, *Journal of Heart and Lung Transplantation*, Apr. 1999, 18(4), 367-71.

Peltier et al., "Treatment practices in heart failure with preserved left ventricular ejection fraction: A prospective observational study", 2007, *International Journal of Cardiology*, vol. 118(3), pp. 363-369.

Pinney et al., "Chronic inotropic therapy in the current era, old wines with new pairings", 2015, *Circ Heart Fail*, vol. 8, pp. 843-846.

Redfield et al., "Effect of phosphodiesterase-5 inhibition on exercise capacity and clinical status in heart failure with preserved ejection fraction: A randomized clinical trial", 2013, *JAMA*, vol. 309(12), pp. 1268-1277.

Seino et al., "Multicenter, double-blind study of intravenous milrinone for patients with acute heart failure in Japan," *Critical Care Medicine*, Sep. 1996, vol. 24(9), pp. 1490-1497.

Seino et al., "Hemodynamic effects and pharmacokinetics of oral milrinone for short-term support in acute heart failure" *Cardiology*, 1995, vol. 86, pp. 34-40.

Sharma et al., "Heart failure with preserved ejection fraction: mechanisms, clinical features and therapies", 2014, *Circulation Research*, vol. 115, pp. 79-96.

Siegel and Rathbone, "Overview of controlled release mechanisms," which is Chapter 2, pp. 19-43 of J. Siepmann, et al. (eds.)

(56) References Cited

OTHER PUBLICATIONS

*Fundamentals and Applications of Controlled Release Drug Delivery. Advances in Delivery Science and Technology*, DOI 10.1007/978-1-4614-0881-9_2, © Controlled Release Society 2012.

Timmis, et al., "Milrinone in heart failure—Acute Effects on left ventricular systolic function and myocardial metabolism," British Heart Journal, vol. 54, No. 1, pp. 36-41 (1985).

Wong, Haishan, The application of Milrinone in respiratory diseases, *Chinese Medical Journal of Metallurgical Industry*, 2010, vol. 27(3), pp. 251 (Chinese and inhouse translation into English).

Wright et al., "Milrinone in the treatment of low output states following cardiac surgery," *European Journal of Anaesthesiology*, 1992, vol. 5:21-6.

Yancy et al., "2013 ACCF/AHA Guideline for the management of heart failure: A report of the American College of Cardiology Foundation/American Heart Association task force on practice guidelines", 2013, *Circulation*, vol. 128,pp. e240-e327.

Zewail, et al., "Intravenous milrinone in treatment of advanced congestive heart failure," Texas Heart Institute Journal, from the Texas Heart Institute of St. Luke's Episcopal Hospital, Texas Children's Hospital, vol. 30, No. 2, pp. 109-113 (2003).

Second Office Action for CN Application No. 201280050932.6 dated Jun. 3, 2016 in 4 pages, w/translation in 5 pages.

Extended European Search Report for Application No. 12824391.2-1464 dated Mar. 11, 2015 in 7 pages.

Extended European Search Report for Application No. 15871347.9-1109 dated Jul. 11, 2018 in 11 pages.

International Preliminary Report on Patentability for Application No. PCT/AU2012/000967 dated Feb. 18, 2014 in 5 pages.

International Search Report for PCT/AU2015/050820 dated Feb. 5, 2016 in 4 pages.

International Preliminary Report on Patentability for Application No. PCT/AU2015/050820 dated Aug. 2, 2016 in 4 pages.

Japanese Office Action dated Mar. 24, 2016 for Japanese Patent Application No. JP 2014-525260 in 7 pages.

Paulus, et al. "How to diagnose diastolic heart failure: a consensus statement on the diagnosis of heart failure with normal left ventricular ejection fraction by the Heart Failure and Echocardiography Associations of the Euromean Society of Cardioloay" *European Heart Journal* (2007):28:2539-2550.

Chinese Heart Failure Guidelines "Guidelines for the Diaonosis and Treatment of Chronic Heart Failure" *Chin J Cardiol.* (2007) 35(12):1076-1095.

Lewis et al. "Biological Phenotypes of Heart Failure with Preserved Ejection Fraction" *Journal of the American College of Cardiology* (2017), 70(17) 2186-2200.

Xuesheng Luo et al."Clinical Observation on Milrinone Treatment to Aged Diastolic Heart Failure", Chinese Journal of Current Clinical Medicine, 2011, 9(3), 148-150, Abstract Only. (Year: 2011).

Marjan Mujib et al. "Angiotensin-Converting Enzyme Inhibitors and Outcomes in Heart Failure and Preserved Ejection Fraction", The American Journal of Medicine, 2013, 126(5), 401-410. (Year: 2013).

Shannan K. Hamlin et al., "Role of Diastole in Left Ventricular Function, II: Diagnosis and Treatment", American Journal of Critical Care, Nov. 2004, 13(6), 453-466. (Year: 2004).

Aisling J. Carroll, etc., "Restrictive Cardiomyopathy With Preserved Ejection Fraction: Outcomes of Lnotropic Support", Journal of the American College of Cardiology, 2009, 53(10), Supp. S. A 159. (Year: 2009).

Wang Jun and Wang Minghe, Diastolic Heart Failure, Chinese Journal of Postgraduates of Medicine; vol. 29, No. 1; pp. 69-71, 2006] has been Raised by the Chinese Patent Office (CNIPA) in Respect of Chinese Application No. 2015800762154.

\* cited by examiner
‡ imported from a related application

METHOD OF TREATING HEART FAILURE WITH PRESERVED EJECTION FRACTION BY ADMINISTERING MILRINONE

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57. This application claims priority to U.S. patent application Ser. No. 15/538,123, filed on Jun. 20, 2017, which claims the benefit of PCT Application No. PCT/AU2015/050820, filed on Dec. 21, 2015, and Australian Provisional Patent Application No. 2014905194, filed on Dec. 22, 2014, all of which are hereby incorporated by reference in their entirety.

BACKGROUND

Field

The present invention relates to methods of treating subjects having heart failure with preserved ejection fraction (HFpEF) with a sustained-delivery formulation of cardiotonic 5-(pyridinyl)-2(1H)-pyridinone compounds.

Description of the Related Art

Bibliographic details of publications referred to in this specification are collected alphabetically at the end of the description.

The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavor to which this specification relates.

Heart failure (HF) is a complex disease state broadly defined by an inability of the heart to pump sufficiently to cope with its venous return and/or to deliver sufficient output to meet the metabolic demands of the body. Severe heart failure is an increasingly common, life-threatening cardiovascular disorder, characterized by marked disability, frequent hospitalization and high mortality. HF is increasingly prevalent in older individuals (up to 10% of the population) and it has become the most common cause for hospitalization in people >65 yrs. HF is a leading cause or contributor to hospitalization and therefore is emerging as a substantial contributor to healthcare spending. The particular clinical manifestations of HF are determined by the underlying cause of the heart failure.

The term heart failure (HF) refers broadly to a pathophysiologic disorder in which cardiac performance is incapable of delivering sufficient blood to meet metabolic demand (e.g. during physical activity or in severe cases at rest), or to accommodate venous return. A range of further sub-classifications can then be applied, however in the commonest clinical paradigm HF is considered according to symptoms of reduced cardiac output leading to easy fatigue and organ dysfunction (e.g. renal), and to symptoms related to congestion either in the lungs (causing breathlessness) or peripherally (leading to swelling of the lower limbs and abdomen). F F is the most common chronic cardiovascular disorder. In the US approximately 5,000,000 patients have heart failure and of these up to 15-20% have the most advanced forms. It is particularly prevalent in older individuals (up to 10% of the general population >70 yrs) and it has become the most common cause for hospitalization in people >65 yrs. Recurrent hospitalization is frequent, with 25% of patients re-admitted within one month of an admission and >50% will be re-admitted within 6 months. The average US cost of an HF admission is >$20,000, with an average length of stay of four to five days.

Many patients suffering from HF have impaired left ventricular (LV) myocardial function. However, HF may be associated with a wide variety of LV dysfunctions. These range from patients with normal LV size and preserved ejection fraction to those with severe dilation of LV and/or markedly reduced ejection fraction (Yancy et al).

Ejection fraction (EF) is considered an important classification in heart failure patients because of patient demographics, comorbid conditions, prognosis and response to therapies and the patients for clinical trials are often selected on the basis of EF (Yancy et al).

HF with reduced EF (HFrEF) has an EF or <40%. Randomised controlled therapeutic trials mainly enroll patients with HFrEF and it is only these patients that have efficacious therapies to date (Yancy et al).

HF with preserved EF (HFpEF) refers to patients having an EF of >40%, with those having an EF from 40 to 49% being considered borderline HFpEF. Several criteria have been proposed to define or diagnose HFpEF including:
  i. clinical signs and symptoms of HF;
  ii. evidence of preserved or normal LVEF; and
  iii. evidence of LV diastolic dysfunction that can be determined by Doppler echocardiography or cardiac catheterization.

At present, in contrast to HFrEF there are no efficacious therapies for HFpEF (Yancy et al, Loffredo et al).

For patients with advanced HFrEF that require hospitalization, the use of positive inotropes such as intravenous dobutamine and milrinone, to stimulate cardiac contraction is common. Recently an oral controlled-release formulation for treating such patients has been developed (WO 2013/023250). Furthermore, the use of long-term inotropic support for "no option" patients, that is, those patients not suitable for heart transplantation or artificial heart transplant, has recently been advocated by the American Heart Association Guidelines for treatment of FIFrEF.

A number of therapies for FIFpEF have been proposed (Kamajda and Lam, Sharma and Kass) including β-blockers and calcium channel blockers, ACE inhibitors and angiotensin receptor blockers and digoxin, each with little or no conclusive benefit. A recent study with spironolactone (Edelmann et al), an aldosterone receptor blocker improved left ventricular diastolic function but did not affect maximal exercise capacity, patient symptoms or quality of life in FIFpEF patients. Another recent study with the phosphosiesterase-5 inhibitor sildenafil (RELAX study) did not result in improvement in exercise capacity or clinical status in FIFpEF patients (Redfield et al). A clinical trial with Ranolazine, a selective inhibitor of late sodium current, also did not result in a change in echocardiographic parameters or exercise performance in HFpEF patients (Komajda and Lam). Some new approaches have had come promising effects in preclinical or early clinical studies, including neprilysin inhibitors, soluble guanylate cyclase stimulators and advanced glycation end products, but have not been yet fully investigated.

Inotropes have not been investigated in HFpEF patients because contractile function is generally thought to be normal or only mildly reduced. Hence those treating heart failure patients would not recommend the use of drugs such as milrinone to treat HFpEF patients based on present literature.

There is a need for therapies that improve one or more of the clinical symptoms of HFpEF.

SUMMARY

The present invention is predicated, at least in part, by the discovery that controlled-release Milrinone is effective in improving the clinical symptoms of patients with HFpEF.

In a first aspect of the present invention, there is provided a method of treating a patient having heart failure with preserved ejection fraction (HFpEF) comprising administering to the patient a sustained-delivery formulation of a 5-(pyridinyl)-2(1H)-pyridinone compound of formula (I):

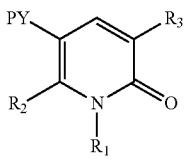

(I)

wherein Ri is hydrogen, -Ci-C$_6$alkyl or -Ci-C$_6$alkyl-OH;
  $R_2$ is -Ci-Cealkyl;
  R is hydrogen, —NH2, —CN, —(O)NH$_2$, halo, —NH(Ci.C$_6$alkyl), —N(Ci.C 6alkyl)2, —NH(COCi-C$_6$alkyl), —CO$_2$H or —CO$_2$Ci-C alkyl; and
  PY is 4-, 3- or 2-pyridinyl optionally substituted with one or two Ci-C$_6$alkyl groups;
  or a pharmaceutically acceptable salt thereof;
wherein the formulation permits delivery of the compound of formula (I) in an amount to achieve steady state plasma levels effective to alleviate the symptoms of FIFpEF;
wherein delivery of the compound of formula (I) is in the range of between 0.1 µ/kg body weight per minute to 20 µ/kg body weight per minute.

In another aspect, the present invention further provides a sustained-delivery formulation of a 5-(pyridinyl)-2(1H)-pyridinone compound of formula (I):

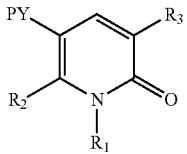

(I)

wherein Ri is hydrogen, -Ci-C$_6$alkyl or -Ci-C$_6$alkyl-OH;
  $R_2$ is -Ci-C$_6$alkyl;
  $R_3$ is hydrogen, —NH$_2$, —CN, —C(O)NH$_2$, halo, —NH(Ci.C$_6$alkyl), —N(Ci.C$_6$alkyl)$_2$, —NH(COCi-C$_6$alkyl), —CO$_2$H or —CO$_2$Ci-C alkyl; and
  PY is 4-, 3- or 2-pyridinyl optionally substituted with one or two Ci-C$_6$alkyl groups;
  or a pharmaceutically acceptable salt thereof;
  wherein the formulation permits delivery of the compound of formula (I) in an amount to achieve steady state plasma levels effective to alleviate the symptoms of HFpEF;
  wherein delivery of the compound of formula (I) is in the range of between 0.1 µ/kg body weight per minute to 20 µ/kg body weight per minute for use in the treatment of heart failure with preserved ejection fraction (HFpEF).

In a further aspect, the present invention also provides use of a sustained-delivery formulation of a 5-(pyridinyl)-2(1H)-pyridinone compound of formula (I):

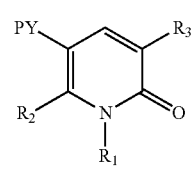

(I)

wherein Ri is hydrogen, -Ci-C$_6$alkyl or -Ci-C$_6$alkyl-OH;
  $R_2$ is -Ci-Cealkyl;
  $R_3$ is hydrogen, —NH$_2$, —CN, —C(O)NH$_2$, halo, —NH(Ci.C$_6$alkyl), —N(Ci.C$_6$alkyl)$_2$, —NH(COCi-C$_6$alkyl), —CO$_2$H or —CO$_2$Ci-C$_6$alkyl; and
  PY is 4-, 3- or 2-pyridinyl optionally substituted with one or two Ci-C$_6$alkyl groups;
  or a pharmaceutically acceptable salt thereof;
wherein the formulation permits delivery of the compound of formula (I) in an amount to achieve steady state plasma levels effective to alleviate the symptoms of HFpEF;
wherein delivery of the compound of formula (I) is in the range of between 0.1 g/kg body weight per minute to 20 g/kg body weight per minute
in the manufacture of a medicament for use in the treatment of heart failure with preserved ejection fraction (HFpEF).

In a yet further aspect the invention further provides the use of a sustained-delivery formulation o 5-(pyridinyl)-2(1H)-pyridinone compound of formula (I):

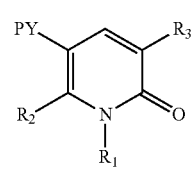

(I)

wherein Ri is hydrogen, -Ci-C$_6$alkyl or -Ci-C$_6$alkyl-OH;
  $R_2$ is -Ci-Cealkyl;
  $R_3$ is hydrogen, —NH$_2$, —CN, —C(O)NH$_2$, halo, —NH(Ci.C$_6$alkyl), —N(Ci.C$_6$alkyl)$_2$, —NH(COCi-C$_6$alkyl), —CO$_2$H or —CO$_2$Ci-C$_6$alkyl; and
  PY is 4-, 3- or 2-pyridinyl optionally substituted with one or two Ci-C$_6$alkyl groups;
  or a pharmaceutically acceptable salt thereof;
wherein the formulation permits delivery of the compound of formula (I) in an amount to achieve steady state plasma levels effective to alleviate the symptoms of HFpEF;
wherein delivery of the compound of formula (I) is in the range of between 0.1µ/kg body weight per minute to 20 µ/kg body weight per minute, in the treatment of heart failure with preserved ejection fraction (HFpEF).

In yet another aspect the invention further provides a method of preparing a sustained-delivery formulation of a 5-(pyridinyl)-2(1H)-pyridinone compound of formula (I):

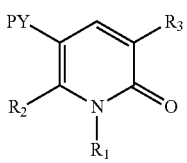

(I)

Wherein Ri is hydrogen, -$C_1$-$C_6$alkyl or -$C_1$-$C_6$alkyl-OH;
$R_2$ is -$C_1$-$C_6$alkyl;
$R_3$ is hydrogen, —$NH_2$, —CN, —$C(O)NH_2$, halo, —NH($C_1$.$C_6$alkyl), —N($C_1$.$C_6$alkyl)$_2$, —NH(CO$C_1$-$C_6$alkyl), —$CO_2H$ or —$CO_2C_1$-$C_6$ alkyl; and
PY is 4-, 3- or 2-pyridinyl optionally substituted with one or two $C_1$-C6alkyl groups;
or a pharmaceutically acceptable salt thereof;
wherein the formulation permits delivery of the compound of formula (I) in an amount to achieve steady state plasma levels effective to alleviate the symptoms of HFpEF;
wherein delivery of the compound of formula (I) is in the range of between 0.1 g/kg body weight per minute to 20 g/kg body weight per minute, for the treatment of heart failure with preserved ejection fraction (HFpEF)
comprising formulating a 5-(pyridinyl)-2(1H)-pyridinone compound of formula (I) as hereinbefore defined with one or more polymers to provide an extended release matrix formulation; and
testing to confirm that the formulation provides the desired release profile for the compound of formula (I).

In some embodiments, the sustained-delivery formulation is a formulation suitable for intravenous administration. In other embodiments, the sustained delivery formulation is an oral controlled-release formulation.

In some embodiments, the patient has an ejection fraction of >50%.

In one embodiment of the invention the compound of formula (I) is 1,2-dihydro-3-cyano-6-methyl-5-(4-pyridinyl)-2(1H)-pyridinone (Milrinone).

DETAILED DESCRIPTION

Definitions

Unless defined otherwise, all technical and scientific terms used herein have the same meaning as commonly understood by those of ordinary skill in the art to which the invention belongs. Although any methods and materials similar or equivalent to those described herein can be used in the practice or testing of the present invention, preferred methods and materials are described. For the purposes of the present invention, the following terms are defined below.

The articles "a" and "an" are used herein to refer to one or to more than one (i.e. to at least one) of the grammatical object of the article. By way of example, "an element" means one element or more than one element.

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

The term "sustained-delivery formulation" as used herein refers to a formulation that is capable of delivering the compound of formula (I) to a patient over a sustained length of time. The formulation may be a formulation for intravenous delivery in which the compound of formula (I) is delivered over a period of hours, days or weeks. The sustained-delivery formulation may be a "controlled-release formulation" formulation.

The term "controlled-release formulation" refers to a formulation in which the compound of formula (I) is administered as a bolus dosage but the formulation releases the drug in a controlled manner. The objective of a controlled-release formulation is to provide zero order kinetics of drug delivery (i.e. a linear delivery with respect to time). Controlled release of drug from the dosage form relies upon two processes: dissolution and release.

As used herein, the term "heart failure with preserved ejection fraction" (HFpEF) refers to heart failure in which the ejection fraction (EF) is ≥40%, with those having an EF from 40 to 49% being considered borderline FIFpEF.

As used herein, the term "heart failure with reduced ejection fraction" (FIFrEF) refers to heart failure in which the ejection fraction (EF) is ≤40%.

As used herein, the term "alkyl" refers to a straight chain or branched saturated hydrocarbon group having 1 to 6 carbon atoms. Where appropriate, the alkyl group may have a specified number of carbon atoms, for example, which includes alkyl groups having 1, 2, 3, 4, 5 or 6 carbon atoms in a linear or branched arrangement. Examples of suitable alkyl groups include, but are not limited to, methyl, ethyl, ˆ-propyl, /-propyl, n-butyl, /-butyl, t-butyl, «-pentyl, 2-methylbutyl, 3-methylbutyl, 4-methylbutyl, «-hexyl, 2-methylpentyl, 3-methylpentyl, 4-methylpentyl, 5-methylpentyl, 2-ethylbutyl and 3-ethylbutyl.

As used herein, the term "halogen" or "halo" refers to fluorine (fluoro), chlorine (chloro), bromine (bromo) and iodine (iodo).

As used herein, the term "pyridine" or "pyridinyl" refers to a 6-membered aromatic cyclic group having one nitrogen atom in the ring having the formula:

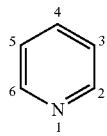

The pyridine ring may be attached to the structure of formula (I) where indicated with the PY at any of the carbon atoms at the 2-, 3- or 4-position.

The compounds of formula (I) may be in the form of pharmaceutically acceptable salts. Suitable pharmaceutically acceptable salts include, but are not limited to, salts of pharmaceutically acceptable inorganic acids such as hydrochloric, sulphuric, phosphoric, nitric, carbonic, boric, sulfamic and hydrobromic acids, or salts of pharmaceutically acceptable organic acids such as acetic, propionic, butyric, tartaric, maleic, hydroxymaleic, fumaric, citric, lactic, mucic, gluconic, benzoic, succinic, oxalic, phenylacetic, methanesulphonic, toluenesulphonic, benzenesulphonic, salicylic, sulphanilic, aspartic, glutamic, edetic, stearic, palmitic, oleic, lauric, pantothenic, tannic, ascorbic and valeric acids.

Base salts include, but are not limited to, those formed with pharmaceutically acceptable cations, such as sodium, potassium, lithium, calcium, magnesium, ammonium and alkylammonium.

Basic nitrogen-containing groups may be quaternized with such agents as lower alkyl halide, such as methyl, ethyl, propyl and butyl chlorides, bromides and iodides, dialkyl sulfates like dimethyl and diethylsulfate, and others.

The term "subject" generally means a human. However, the present invention extends to the treatment of animal model systems including non-human primates as well as pigs, sheep, dogs and horses. Non-human commercial applications include the treatment of race animals such as horses, dogs and camels as well as work animals such as horses and dogs. By "human" means a person of any age from infant, child, adolescent, teenager, young adult, adult, middle age and aging individual. Age ranges from 1 day old to 120 years old are contemplated herein. In extreme emergencies, in utero treatments of unborn babies may be contemplated and is encompassed by the present invention.

Methods

The present invention relates to methods of treating patients with HFpEF with a compound of formula (I). In one aspect the invention relates to a method of treating patients with HFpEF with a sustained-delivery formulation of a compound of formula (I) wherein the formulation permits delivery of the compound of formula (I) in an amount to achieve steady state plasma levels effective to alleviate the symptoms of FIFpEF; wherein delivery of the compound of formula (I) is in the range of between 0.1μ/kg body weight per minute to 20 μ/kg body weight per minute.

In some embodiments, the patients with HFpEF are patients having borderline HFpEF (an ejection fraction between >40 and 49%). In other embodiments, the patients with HFpEF are patients having an ejection fraction of ≥50%.

The administration is generally under conditions sufficient to achieve levels of the compound of formula (I) which are not overly toxic and which is effective to alleviate the symptoms of HFpEF. Conveniently, the compound of formula (I) is formulated to enable compound delivery into the blood stream at a rate of between above 0.^g/kg body weight/minute to about 20 μg/kg body weight/minute. This range includes 0.1, 0.2, 0.3, 04, 0.5, 0.6, 0.7, 0.8, 0.9, 1, 2, 3, 4, 5, 6, 7, 8, 9, 10, 11, 12, 13, 14, 15, 16, 17, 18, 19 and 20 μg/kg body weight/minute as well as fractions in between. In a particular embodiment, the compound of formula (I) is delivered at a rate of from about 0.3 to ^g/kg body weight/minute including from about 0.37 to 0.75 μg/kg body weight/minute.

The amount of compound of formula (I) that is administered will depend on the subject being treated, their physical condition, their weight and the formulation being used. Suitable oral dosages are in the range of 5 mg to 75 mg, especially 10 to 50 mg or 10 to 40 mg. Suitable intravenous dosing includes administration in the range of 0.1 to 0.75 μg/kg/min as a continuous infusion.

When in the form of an oral controlled-release dosage form, the dosage may be provided in a single dose per day, for example, one dose of 30 to 40 mg, or may be provided in divided dosages for example, two, three or four times a day. Amounts 15 to 30 mg or 15 to 20 mg every 12 hours is a useful therapeutic amount in accordance with the present invention and allows for 12 hourly or twice daily dosing. Amounts of 10 to 15 mg every 8 hours allows for dosing three times per day and amounts of 7.5 to 10 mg every 6 hours allows for dosing four times a day. In particular embodiments, administration is twice daily.

The optimal plasma level of a compound of formula (I) such as milrinone, is in the range of 100 ng/mL to 400 ng/mL, especially 100 ng/mL to 300 ng/mL. Plasma clearance of the compound of formula (I) is affected by the presence of either renal or cardiovascular disease. The optimal dose of sustained-delivery compound of formula (I) may need to be determined for an individual patient by a stepwise upward titration of the dose accompanied by regular monitoring of the patient's plasma levels of compound of formula (I) until the required steady state level is achieved. In some embodiments, the method further comprises the step of monitoring plasma concentrations of the compound of formula (I) and if necessary, adjusting the dosage to achieve a plasma concentration in the range of 100 to 400 ng/mL.

In some embodiments, in the compound of formula (I), at least one of the following applies: $R_i$ is selected from hydrogen, -$C_i$-$C_3$alkyl or -$C_i$-$C_3$alkylOH, especially hydrogen, —$CH_3$ or —$CH_2OH$, more especially hydrogen; $R_2$ is selected from -$C_i$-$C_3$alkyl, especially methyl or ethyl, more especially methyl; $R_3$ is selected from —CN (cyano), —$NH_2$, halo, —NH($C_i$-$C_3$alkyl), —N($C_i$-$C_3$alkyl)$_2$, —$CO_2H$ or —$CO_2C_i_3$alkyl, especially —CN, —$NH_2$, —$CO_2H$ and —$CO_2CH$, more especially —CN; and PY is unsubstituted 4-, 3- or 2-pyridinyl, especially unsubstituted 4-pyridinyl.

In a particular embodiment, the compound of formula (I) is 1,2-dihydro-3-cyano-6-methyl-5-(4-pyridinyl)-2(1H)-pyridinone. This compound is also known as 2-methyl-6-oxo-dihydro-3,4'-bipyridine-5-carbonitrile and milrinone.

Methods of making compounds of formula (I) including milrinone are known in the art and can be found, for example, in GB Patent No. 2065642 and U.S. Pat. No. 4,313,951.

In some embodiments, the intravenous administration may be a continuous intravenous infusion administered over a period of 1 to 48 hours, but is not limited to this period.

In other embodiments, the sustained-delivery formulation is an oral controlled-release formulation. In some embodiments, the oral controlled-release formulation comprises: i) a core comprising the compound of formula (I) and one or more polymers and one or more excipients; and ii) a sustained-release coating.

The compound of formula (I) may be blended with one or more polymers, to provide a matrix that is either formed into a particle (small or large), or is coated on an inert particle to form the core of the formulation. The polymers of the core are selected from hydrophilic, hydrophobic or plastic. Hydrophilic polymers are water soluble and hydrate in contact with water to form a hydrogel as they dissolve and swell; hydrophobic polymers do not dissolve but may be subject to erosion as the matrix releases soluble constituents; plastic polymers form insoluble or skeletal matrices but do not erode. Upon exposure to the fluid in the stomach, small intestine and colon, hydrophilic polymers hydrate and form a hydrogel that acts as a diffusion barrier to drug release; hydrophobic polymers release drug through diffusion through pores and through erosion. Drug release from plastic matrices is controlled by the rate of liquid penetration and is accelerated by the presence of channel forming agents: soluble components that are added in addition to drug.

The behaviour of some polymers is dependent upon pH. This is particularly true where the polymer contains acidic or basic moieties as pH will affect the ionization state. Ionization can transform a polymer from hydrophobic to hydrophilic, with an accompanying transformation in release properties.

The release of the dissolved compound of formula (I) into, for example, the gastrointestinal (GI) tract may also be controlled by the coating on the particle. This coating is typically a polymer or blend of polymers that is relatively stable towards the conditions encountered in the gut. In many cases, the coating includes at least one hydrophilic polymer that will swell on contact with fluid in the gut to form a hydrogel barrier that is homogenous and stable to changes that may take place to the underlying matrix. The hydrogel also assists with slow release of dissolved compound of formula (I). The properties of the surface coating can be pH dependent depending upon the presence of acidic or basic moieties in the polymer constituents.

A particular disadvantage of some controlled-release formulations is the potential for a burst release of drug to occur immediately following contact of the dosage form with the dissolution fluid. The use of a hydrophilic polymer in the film coating or in the matrix, wherein the hydrophilic polymer forms a hydrogel rapidly after hydration, can significantly reduce the incidence of the burst release phenomenon.

Controlled-release oral formulations include a monolithic tablet dosage form in which one or more drug-polymer matrices provide the core and or particulate or bead dosage forms in which an inert particle coated with drug provides the core. These types of formulations may include an optional surface film coating to provide additional control over drug release. Particulate dosage forms may be formed into a tablet or filled into a capsule. This differs from immediate release (TR) formulations which are designed to disintegrate, dissolve promptly and release a bolus dose of drug.

The core matrix containing the compound of formula (I) may be formed by granulation or direct compression and may be heterogeneous to provide porosity.

In particular, a core matrix may comprise either or both hydrophilic polymers and hydrophobic polymers in order to achieve the appropriate release profile. Further, one or more of the polymers may swell upon hydration in a manner that may additionally be dependent upon pH, to form a hydrogel that is viscous and gelatinous and thus provides a barrier to drug release. The composition of hydrogel determines its properties, which can thus be manipulated in order to achieve appropriate drug release kinetics.

The optional surface film coating provides a diffusion release mechanism where the permeability is often directly related to hydration leading to polymer swelling and the installation of hydrogel dynamics.

At least one combination of matrix and optional surface film coating provided in the description below can be used in the formulation of the invention to achieve the desired release profile across the different environments encountered during transit through the GI tract.

Sustained release formulations of compounds of formula (I), and in particular sustained release formulations of milrinone, which achieve the desired release profile across the different environments encountered during transit through the GI tract are described in PCT application PCT/AU2012/000967, published as WO 2013/023250 A1. The release profile of a sustained release formulation of a compound of formula (I) can be determined in accordance with the dissolution study methods described in WO 2013/023250 A1 and as described in the Examples below. A sustained-release formulation of a compound of formula (I) preferably provides zero order kinetics of drug delivery (i.e. a linear delivery with respect to time).

The invention further provides a method of preparing a sustained-delivery formulation of a 5-(pyridinyl)-2(1H)-pyridinone compound of formula (I) as hereinbefore defined, or a pharmaceutically acceptable salt thereof; wherein the formulation permits delivery of the compound of formula (I) in an amount to achieve steady state plasma levels effective to alleviate the symptoms of HFpEF; wherein delivery of the compound of formula (I) is in the range of between 0.1 µ/kg body weight per minute to 20 µ/kg body weight per minute, for the treatment of heart failure with preserved ejection fraction (HFpEF) comprising the steps of:
  formulating a 5-(pyridinyl)-2(1H)-pyridinone compound of formula (I) as hereinbefore defined with one or more polymers to provide an extended release matrix formulation; and
  testing to confirm that the formulation provides the desired release profile for the compound of formula (I).

In some embodiments the sustained-delivery formulation is for oral administration. In some embodiments the compound of formula (I) is formulated with one or more pharmaceutical excipients. In some embodiments the compound of formula (I) is formulated as a core comprising the compound of formula (I) and one or more polymers and one or more pharmaceutically acceptable excipients and a sustained release coating. In some embodiments the formulation is provided with one or more seal coatings. In some embodiments the formulation is provided with one or more enteric coatings. In some embodiments the compound of formula (I) is formulated as a unit dose form, for example as a minitablet or as beads. In some embodiments the sustained-delivery formulation is a composition as herein defined. In some embodiments, the sustained delivery formulation comprises: iii) a core comprising the compound of formula (I) and one or more polymers and one or more excipients; and iv) a sustained-release coating.

In a particular embodiment the sustained delivery formulation comprises a compound of formula (I) in a polymeric matrix, the polymeric matrix and compound of formula (I) mixture having a seal coating. The seal-coated polymeric matrix compound of formula (I) has a sustained-release coating and the formulation further comprises an enteric-release coating. Optionally, there is a buffer-coating between the sustained-release coating and the enteric-release coating.

Methods of testing to confirm that the formulation provides the desired release profile of the compound of formula (I) are known in the art and may include dissolution or release studies such as those described herein. Preferably the sustained delivery formulation provides zero order kinetics of drug delivery (i.e. a linear delivery with respect to time).

Polymers that are of use in the formation of core drug-polymer matrices are as follows:
  Acrylic and methacrylic polymers including hydroxypropyl methacrylates (HPMA) and hydroxyethyl methacrylates (HEMA), as well as N-isopropyl acrylamides;
  Polyethylene oxides (PEO) also known as polyethylene glycols (PEG) and polypropylene oxides (PPO), as well as block copolymers of PEO and PPO (also known as Pluronics (Registered Trade Mark);
  Cellulose ethers including hydroxypropyl methylcellulose (HPMC), hydroxypropylcellulose (HPC), hydroxyethyl cellulose (HEC), methylcellulose (MC), ethyl cellulose (EC) and carboxymethylcellulose (CMC);
  Polylactides (PLA), polyglucolides (PGA), copolymers of polylactide and polyglucolide in various proportions (PLGA);
  Poly(sucrose acrylates);
  Polylysine, polyvinyl amine, polyethylimine (PEI), polyglutamic acid, polyvinyl alcohol (PVA); copolymers of ethylene and vinyl acetate (pEVA);
  Polyethyleneglycol terephthalate, polybutylene terephthalate and copolymers thereof (also known as Locteron [Registered Trade Mark]); Copolymers of PEG and PLGA also known as Re-Gel (Registered Trade Mark); Polyorthoesters also known as Chronomer (Registered Trade Mark); polyanhydrides; copolymers of acrylic acids and esters, or methacrylic acids and esters of various molecular weight and proportion also known as Eudragit (Registered Trade Mark) in particular RL30D, RLPO, RL100, RS30D, RSPO, RS100, E30D, M30D, E40D, L100; copolymers of phthalic acid cellulose and phthalic ester cellulose also known as CAP (Registered Trade Mark);

Polyvinylpyrrolidone also known as Kollidon (Registered Trade Mark) and copolymers thereof with polyvinyl acetate also known as Kollidon SR (Registered Trade Mark)'

Polymers of natural origin including non-ionic, amino, carboxylated and sulfated polysaccharides, optionally chemically modified through partial hydrolysis and/or conjugation of modifiers such as carboxylates or long chain fatty acids (C8-C16), include:

Guar gum; acacia gum, tragacanth gum, xanthan gum, carrageenans (both iota and lambda), Linn gum, alginates, scleroglucans, dextrans, chitins and chitosans, pectins, galactomannans including locust bean gum.

In addition, it is frequently found that polymer blends are particularly useful for providing the appropriate release profiles for controlled-release formulations, for example mixing polymers with hydrophilic and hydrophobic properties, and such polymer blends would include:

Methyl methacrylates polymers with starch or cellulose polymers;

Polyacrylic acid-Pluronic-polyacrylic acid block copolymers;

Multilayer polyelectrolytes using cationic polymers selected from chitosan, polylysine, polyallylamine or polyvinylamine with anionic polymers selected from Carbopols including 97 INF, carrageenan, xanthan gum, alginate, hyaluronic acids, Eudragit® including L100 and carboxymethylcellulose;

Hydrophobic cellulose polymers such as ethylcellulose or Compritol 888 ATO are often mixed with hydrophilic polymers such as HPMC, NaCMC, sodium alginate, xanthan gum or Methocel (Registered Trade Mark);

Hydrophilic swelling polymer such as HPMC is mixed with a pH dependant polymer such as Eudragit (Registered Trade Mark) L100-55;

Polymer blends may be crosslinked either by covalent bonds or, particularly for polymers of natural origin, through the addition of polyvalent cations including borate, calcium, magnesium and zinc;

Natural gums are often used in polymer blends, in particular carrageenans with cellulose ethers, xanthan gum with locust bean gum.

Whilst ternary blends are less common, one example is a blend of non-ionic water soluble polymer Polyox with a swellable high molecular weight crosslinked acrylic polymer Carbopol and lactose.

Film coatings are contemplated for use with multi-unit dosage forms other than monolithic tablets. Coatings are selected which include polymer, solvent and a plasticiser, particularly triethyl citrate, dibutyl sebacate, diethyl phthalate or propylene glycol. Plasticisers may not be necessary when poly(dimethylsiloxane) or other silane elastomers are used.

Particular examples of surface coatings which can provide a hydrogel barrier upon hydration include the cellulose polymers, Eudragit (Registered Trade Mark) polymers and graft copolymers of polyvinyl acetate, polyvinyl alcohol and PEG, also known as Kollicoat (Registered Trade Mark), for example Kollicoat (Registered Trade Mark) SR and Kollicoat (Registered Trade Mark) IR, used with propyleneglycol as plasticiser. The properties of this coating are independent of pH.

Polyelectrolyte multilayers (PEM) are one particular example of a film coating which can provide an appropriate rate of drug release through a combination of variables including:

The selection of positive and negatively charged polyelectrolytes;

The number of layers that are deposited;

The molecular weight of the polyelectrolytes used to form the film.

The permeability of PEMs can be responsive to stimuli whereby a change in pH, ionic strength or temperature has the potential to change the permeability to particular solutes.

Multilayer tablet formulations are particularly useful for highly soluble drugs. Such dosage forms include a hydrophilic matrix core with one or two semipermeable coatings, which may be implemented as a film or compressed barrier. Typical polymers include cellulose derivatives particularly HPMC, NaCMC, HPC, EC or MC, or natural gums particularly tragacanth or guar gum.

In one embodiment, the core comprises a compound of formula (I), hydroxypropylmethylcellulose or hydroxypropylcellulose having a viscosity of 80,000 to 120,000 cps; hydroxypropylmethylcellulose having a viscosity of about 50 cps;

and at least one pharmaceutically acceptable excipient;

wherein the hydroxypropylmethylcellulose or hydroxypropylcellulose (80,000 to 120,000 cps) and the hydroxypropylmethylcellulose (50 cps) are in a ratio of 2:1 to 1:2, and the ratio of compound of formula (I) to total hydroxypropylmethylcellulose or hydroxypropylmethylcellulose and hydroxypropylcellulose is 1:2 to 1:6.

Hydroxypropylmethylcellulose, also known as hypromellose or HPMC, is available in different viscosities. In the present invention, the hydroxypropylmethylcellulose is present in two viscosities, 80,000 to 120,000 cps and about 50 cps. A suitable HPMC having a viscosity of 80,000 to 120,000 is hypromellose 2208 USP which comprises 19-24% methoxy ether substitution and 7-12% hydroxypropyloxy ether substitution on glucose C2, C3 and C6 hydroxyl moieties and has a viscosity of about 100,000 cps. The viscosity is measured at 2% concentration in water at 20° C. A suitable HPMC (80,000 to 120,000) is HPMC K100M. A suitable HPMC having a viscosity of about 50 cps is HPMC E50 LV.

In some embodiments, the HPMC (80,000 to 120,000) may be substituted by hydroxypropylcellulose (HPC) having a viscosity of 80,000 to 120,000 cps.

In some embodiments, the HPMC or HPC (80,000 to 120,000) is HPMC (80,000 to 120,000), especially HPMC K100M.

In some embodiments, the HPMC (about 50 cps) is HPMC E50 LV.

In some embodiments the ratio of HPMC or HPC (80,000 to 120,000) to HPMC (about 50 cps) is in the range of 1.5:1 to 1:1.5, especially about 1:1.

In some embodiments, the ratio of compound of formula (I) to total HPMC or HPMC or HPC (80,000 to 120,000) and HPMC (about 50 cps), is 1:2 to 1:6, especially about 1:3 to 1:5, more especially about 1:3.

In some embodiments the compound of formula (I) is present in an amount of 10 to 30% w/w of the core, especially 15 to 25% w/w of the core, more especially about 20% w/w of the core.

In some embodiments the HPMC or HPC (80,000 to 120,000) is present in an amount of 20 to 40% w/w of the core, especially 25 to 35% w/w of the core, more especially about 30%>w/w of the core.

In some embodiments, the HPMC (about 50 cps) is present in an amount of 10 to 40% w/w of the core, especially 20 to 35% w/w or 25 to 35% w/w of the core, more especially about 30%>w/w of the core.

In some embodiments the core also comprises pharmaceutically acceptable excipients such as binders and/or lubricants. Suitable binders include disaccharides such as sucrose and lactose, polysaccharides such as starches and cellulose derivatives, for example, microcrystalline cellulose, cellulose ethers and hydroxypropylcellulose (HPC), sugar alcohols such as xylitol, sorbitol or maltitol, proteins such as gelatine and synthetic polymers such as polyvinylpyrrolidone (PVP) and polyethylene glycol (PEG). In a particular embodiment, the binder is microcrystalline cellulose.

In some embodiments, the binder is present in an amount of 10 to 30% w/w of the core, especially about 15 to 25% w/w of the core, more especially about 18% w/w of the core. In some embodiments, the compound of formula (I) such as milrinone and the binder such as microcrystalline cellulose are together present in the core in about 30 to 50%, especially about 40% w/w of the core. In some embodiments, the ratio of compound of formula (I) to binder is 1:2 to 2:1, especially about 1:1.

Suitable lubricants include fats such as magnesium stearate, vegetable stearin and stearic acid, talc or silica. In particular embodiments, the lubricant is magnesium stearate.

In some embodiments, the lubricant is present in an amount of 0.5 to 5% w/w of the core, especially about 1 to 3% w/w of the core, especially about 2% w/w of the core.

In another embodiment the core comprises a compound of formula (I), a hydrophilic matrix comprising at least two natural gums, and at least one pharmaceutically acceptable excipient; wherein the two natural gums are in a ratio of 2:1 to 1:2; and the ratio of the compound of formula (I) to the hydrophilic matrix is 1:1 to 1:2.5.

Suitable natural gums include guar gum, acacia gum, tragacanth gum, xanthan gum, carrageenans (both iota and lambda), Linn gum, alginates, scleroglucans, dextrans, chitans and chitosans, pectins, and galactomannans including locust bean gum. In some embodiments the hydrophilic matrix includes xanthan gum or locust bean gum. In a particular embodiment the hydrophilic matrix includes xanthan gum and locust bean gum.

In some embodiments, the ratio of xanthan gum to locust bean gum is about 1.5:1 to 1:1.5, especially about 1:1.

In some embodiments, the ratio of compound of formula (I) to hydrophilic matrix is 1:1 to 1:2, especially about 1:1.5.

In some embodiments, the compound of formula (I) is present in an amount of 15 to 25% w/w of the core, especially 18 to 22% w/w of the core, more especially about 20% w/w of the core.

In some embodiments, the hydrophilic matrix is present in an amount of 20 to 40% w/w of the core, especially 25 to 35% w/w of the core, more especially about 30%>w/w of the core. For a ratio of 1:1 xanthan gum to locust bean gum, the amount of each gum will be about 15%>w/w of the core.

In some embodiments, the excipients are selected from binders, fillers, glidants, lubricants and mixtures thereof.

Suitable binders include disaccharides such as sucrose and lactose, polysaccharides such as starches and cellulose derivatives such as microcrystalline cellulose, cellulose ethers and hydroxypropylcellulose (HPC), sugar alcohols such as xylitol, sorbitol or maltitol, proteins such as gelatine and synthetic polymers such as polyvinylpyrrolidone (PVP) and polyethylene glycol (PEG). In particular embodiment, the binder is microcrystalline cellulose, polyvinylpyrrolidone (PVP) or mixtures of microcrystalline cellulose and PVP.

In some embodiments the binder is present in an amount of 17 to 30%>w/w of the core, more especially about 23.5%>w/w of the core. In some embodiments the binder comprises about 20% w/w of microcrystalline cellulose and about 3.5% w/w PVP.

Suitable fillers or bulking agents include lactose, sucrose, glucose, mannitol, sorbitol, calcium carbonate and dibasic calcium phosphate. In a particular embodiment, the filler is lactose.

In some embodiments, the filler is present in the core in an amount of 20% w/w of the core, especially about 25% w/w of the core.

Suitable glidants include fumed silica, talc and magnesium carbonate. In a particular embodiment, the glidant is fumed silica.

In some embodiments the glidant is present in an amount of about 0.5 to 1.5% w/w of the core, especially about 1% w/w of the core.

Suitable lubricants include fats such as magnesium stearate, vegetable stearin and stearic acid, talc or silica. In particular embodiments, the lubricant is magnesium stearate.

In some embodiments the lubricant is present in an amount of 0.25 to 1% w/w of the core, especially about 0.5% w/w of the core.

In yet another embodiment the core comprises
(i) a coating composition comprising a compound of formula (I), one or more polymers, and one or more excipients, and
(ii) inert spherical particles; wherein the coating composition is on coated on the surface of the spherical particles; wherein the ratio of compound of formula (I) to the spherical particles is about 1:5 to 1:25; and wherein the coated particles further comprise a seal coating.

The inert spherical particles may be any inert spherical particles commonly used in microparticulate systems. Typically, the inert spherical particles have a diameter of 0.06 to 2 mm. Suitable inert spherical particles are sugar and/or starch spherical particles. Such particles are suitable for formulation into a capsule or tablet. Microparticle dosage systems can provide the following benefits for extended release formulations:

Less dependent on gastric emptying, resulting in less intra/inter individual variability in gastric transit time (sizes less than 2 mm are able to continuously leave stomach even when pylorus is closed);

Particles are better distributed, avoiding possibility of localised irritation;

Drug safety is improved for modified release formulations, as less susceptible to performance failure if damaged;

Multiparticulate formulations are popular for selective delivery to the colon when that is the only absorption window, they can also be used for continuous GI absorption. Furthermore it is possible to mix particles with different release profiles to optimise exposure in different regions of gut.

In some embodiments, the compound of formula (I) is prepared in a coating composition comprising a coating polymer and excipients such as binders. The coating composition is then coated onto the spherical particles.

Suitable coating compositions comprise, in addition to compound of formula (I), a polymer, plasticiser and binder. If required, the coating composition may be dissolved or suspended in a suitable solvent, such as water, for application. Suitable polymers include polyvinyl alcohol (PVA) or cellulose polymers such as HPMC, hydroxypropylcellulose (HPC), hydroxyethylcellulose (HEC), methylcellulose (MC), ethylcellulose (EC) and carboxymethylcellulose (CMC). Suitable plasticisers include propylene glycol, polyethylene glycol (PEG), dibutyl sebacate, glycerine, triethyl citrate and diethyl phthalate. In one particular embodiment, the polymer is HPMC and the plasticiser is PEG, for example, the coating composition sold under the trade mark OPADRY CLEAR (Registered Trade Mark). In another particular embodiment, the polymer is PVA and the plasticiser is PEG and/or glycerine, for example, the coating composition sold under the trade mark OPADRY II (Registered Trade Mark).

The coating composition may also comprise a binder. Suitable binders include disaccharides such as sucrose and lactose, polysaccharides such as starches and cellulose derivatives such as microcrystalline cellulose, cellulose ethers and hydroxypropylcellulose (HPC), sugar alcohols such as xylitol, sorbitol or maltitol, proteins such as gelatine and synthetic polymers such as polyvinylpyrrolidone (PVP) and polyethylene glycol (PEG). In a particular embodiment, the binder is PVP.

In some embodiments, the ratio of compound of formula (I) to the polymer/plasticiser blend is about 1.5:1 to 2:1, especially about 1.6:1 to 1.8:1.

In some embodiments, the ratio of compound of formula (I) to binder is in the range of 8:1 to 12:1, especially about 11:1.

In some embodiments, the ratio of compound of formula (I) to spherical particles is about 1:10 to 1:25, especially about 1:15 to 1:20.

Seal Coating/Buffer Coating

In some embodiments, the formulations of the invention may comprise a seal coating. The seal coating may be applied over the core, for example over the drug coating of the spherical particles or may be used as a coating on a tablet formed by compression of the core, also for example between layers of the formulation, such as between the core and the sustained-release coating (seal coat) or between the sustained-release coating and the enteric-release coating (buffer coat). The seal coating or buffer coating may comprise a polymer and a plasticiser. Suitable polymers include PVA and cellulose polymers such as HPMC, hydroxypropylcellulose (HPC), hydroxyethylcellulose (HEC), methylcellulose (MC), ethylcellulose (EC) and carboxymethylcellulose (CMC). Suitable plasticisers include propylene glycol, polyethylene glycol (PEG), dibutyl sebacate, glycerine, triethyl citrate and diethyl phthalate. In a particular embodiment, the polymer is HPMC and the plasticiser is PEG, for example, the coating composition sold under the trade mark OPADRY CLEAR (Registered Trade Mark). In another particular embodiment, the polymer is PVA and the plasticiser is PEG and/or glycerine, for example, the coating composition sold under the trade mark OPADRY II (Registered Trade Mark). The seal coating or buffer coating may also include a pigment to give a desired colour, for example, titanium dioxide to give white. The seal coating or buffer coating may be present in an amount of 3 to 15% w/w of the formulation, especially 5 to 12% w/w, more especially 5 to 10% w/w.

Sustained-Release Coating

The formulations above include a sustained-release coating. Suitable sustained-release coatings include cellulose derivative coatings such as HPMC, HPC, HEC, EC, MC and CMC or co-polymers of acrylic acids and their esters or methacrylic acids or their esters, such as those sold under the trade mark Eudragit® including RL30D, RLPO, RL100, RS30D, RSPO, RS100, E 30D, E40 D and L100. In particular embodiments, the sustained-release coating may comprise ethylcellulose (EC), which is insoluble in water, in which case, the sustained-release coating may optionally include a low content of water soluble polymer such as a low viscosity HPMC (e.g.: 6 cps), for example Opadry Clear™. In other embodiments, the sustained-release coating may comprise an acrylic acid, acrylic ester, methacrylic acid or methacrylic ester optionally including a low content of a methacrylic acid ester with quaternary ammonium groups (trimethylammonioethyl methacrylate chloride) copolymer. This sustained-release coat may be comprised of one or more copolymers of ethyl acrylate (A), methyl methacrylates (B) and a low content of a methacrylic acid ester with quaternary ammonium groups (trimethylammonioethyl methacrylate chloride) (C). For the polymeric materials of this embodiment, the molar ratio of the monomers A:B are in the range 1:1-1:3 preferably 1:2; the molar ratio of the monomers A:C are in the range 1:0.01: to 1:0.5, preferably in the range 0.05-0.25. When one or more of the layers comprises a blend of two copolymers, The molar ratio of the monomers A:B:C in the first of the copolymers is approximately 1:2:0.2 and the molar ratio of the monomers A:B:C in the second of the copolymers is 1:2:0.1, and the ratio of the first and the second copolymer is in the range 1:5 to 1:15, especially about 1:9.

The sustained-release coatings may also comprise lubricants. The sustained-release coatings may also comprise plasticisers. The sustained-release coatings may also comprise anti-tacking agents.

In a particular embodiment, the sustained-release coating comprises ethyl cellulose as Aquacoat ECD 30 and HPMC 6 cps as Opadry Clear wherein the ratio of EC and HPMC is in the range 19:1 to 4:1 especially about 9:1.

In a particular embodiment, the sustained-release coating comprises ethyl cellulose as Aquacoat ECD 30 and HPMC 6 cps as Opadry Clear, and a plasticiser, wherein the ratio of EC and HPMC is in the range 19:1 to 4:1 especially about 9:1 and the ratio of EC to plasticiser is in the range 9:1 to 2:1 especially about 3:1.

In a particular embodiment, the sustained-release coating comprises ethyl cellulose as Aquacoat ECD 30 and HPMC 6 cps as Opadry Clear, and further comprises talc and a plasticiser, wherein the ratio of EC and HPMC is in the range 19:1 to 4:1 especially about 9:1; the ratio of EC to talc is in the range 19:1 to 4:1 especially about 9:1, and the ratio of EC to plasticiser is in the range 9:1 to 2:1 especially about 3:1.

In a particular embodiment, the sustained release coating comprises Eudragit RS30D, Eudragit RL30D or mixtures thereof wherein the ratio of the first and second copolymer is in the range of 1:5 to 1:15, especially about 1:9.

The sustained release coating may be applied to the formulation in tablet form or to the drug-coated spherical particles.

In some embodiments, the formulation may comprise more than one sustained-release coating. In some embodiments, a first sustained release coating may be present followed by a second sustained-release coating. The first and second sustained release coatings may be the same or different. For example, the first coating may be an ethylcellulose coating and the second coating a Eudragit coating such as a combination of Eudragit RS30D and Eudragit RL30D or the first coating may be a combination of Eudragit RS30D and Eudragit RL30D and the second coating may be Eudragit RS30D.

Typically, the sustained-release coatings will be present in an amount of 1 to 40% w/w of the sustained-release coated formulation, especially 3 to 30%, more especially 5 to 25%. In one embodiment, an ethylcellulose coating may be present in an amount of 3 to 15% w/w of the sustained-release coated formulation, especially 5 to 10%>, for example, about 7.5% or may be present in an amount of about 5% w/w of the sustained-release coated formulation. In another embodiment, an ethylcellulose coating may be present in an amount of about 10% w/w of the sustained-release coated formulation. In yet another embodiment, a sustained-release coating of Eudragit RL30D and Eudragit RS30D may be present in an amount of about 25% w/w of the sustained-release coated formulation and may further comprise a sustained-release coating of Eudragit RS30D which may be present in an amount of about 15% w/w of the sustained-release coated formulation.

Enteric-Release Coat

Optionally, any of the formulations above may include an enteric-release coating. Suitable enteric-release coatings include cellulose coatings such as cellulose acetate phthalate polymers or hydroxypropyl methylcellulose phthalate polymers or co-polymers of acrylic acids and their esters or methacrylic acids or their esters, such as those sold under the trade mark Eudragit® including L100, L100-55 and S100. In particular embodiments, the enteric-release coating may comprise poly(methacrylic acid-co-ethyl acrylate) 1:1 (Eudragit L100-55); poly(methacrylic acid-co-ethyl acrylate) 1:1 (Eudragit L100) and methacrylic acid-methyl methacrylate copolymer (1:2) (Eudragit S100). In a preferred embodiment, the enteric release coating is poly(methacrylic acid-co-ethyl acrylate) 1:1 (Eudragit L100-55) or an aqueous dispersion thereof (Eudragit L30 D-55).

The enteric-release coatings may also comprise lubricants. The enteric-release coatings may also comprise plasticisers. The enteric-release coatings may also comprise anti-tacking agents.

In a particular embodiment, the enteric-release coating comprises Eudragit L100-55.

In a particular embodiment, the enteric-release coating comprises Eudragit L100-55 and a plasticiser wherein the ratio of polymer and plasticiser is in the range 19:1 to 4:1 especially about 9:1.

In a particular embodiment, the enteric-release coating comprises Eudragit L100-55, plasticiser and an anti-tacking agent, wherein the ratio of polymer and plasticiser is in the range 19:1 to 4:1 especially about 9:1 and the ratio of polymer to anti-tacking agent is in the range 4:1 to 1:4, preferably 3:1 to 1:3, more preferably 3:2 to 2:3, for example 3:2 or 1:1.

Typically, the enteric-release coatings will be present in an amount of 20-60%>w/w of the enteric-release coated formulation, for example 20 to 50% w/w, especially 25 to 40% w/w, for example about 40% w/w or 30% w/w of the enteric-release coated formulation. In one embodiment, a coating of poly(methacylic acid-co-ethyl acrylate) 1:1 (Eudragit L100-55). may be present in an amount of about 30% w/w of the enteric-release coated formulation.

Formulations

In some embodiments, the formulations of the invention may include further excipients such as dispersants, solvents, preservatives, flavours, microbial retardants and the like. Examples of dispersing agents include vegetable oils, aliphatic or aromatic hydrocarbons (e.g. n-decane, n-hexane etc.), aliphatic or aromatic esters (e.g. octanoate) and ketones. Solvents that are poorly miscible with water, such as dichloromethane, chloroform and fluorinated hydrocarbons are also examples of dispersing agents. The dispersing agents may be removed from the formulation in the process of forming the matrix and/or after preparation of the invention but prior to administration. Suitable preservatives and antimicrobial agents include for example, EDTA, benzyl alcohol, bisulphites, monoglyceryl ester of lauric acid (Monolaurin), capric acid and/or its soluble alkaline salts or its monoglyceryl ester (Monocaprin), edetate and capric acid and/or its soluble alkaline salts or its monoglyceryl ester (Monocaprin) and edetate.

The pharmaceutical compositions used in the methods of the present invention may be formulated and administered using methods known in the art. Techniques for formulation and administration may be found in, for example, *Remington: The Science and Practice of Pharmacy*, Loyd V. Allen, Jr (Ed), The Pharmaceutical Press, London, 22nd Edition, September 2012; *Martindale: The Complete Drug Reference*, Alison Brayfield (Ed), Pharmaceutical press, London, 38th Edition, 2014; and *Handbook of Pharmaceutical Excipients*, Raymond C. Rowe et a/(Eds), Pharmaceutical Press, London, Seventh Edition, 2012 for formulation methods and reagents.

The pharmaceutical forms suitable for intravenous use include sterile injectable solutions or dispersions, and sterile powders for the extemporaneous preparation of sterile injectable solutions. They should be stable under the conditions of manufacture and storage and may be preserved against reduction or oxidation and the contaminating action of microorganisms such as bacteria or fungi.

The solvent or dispersion medium for the intravenous solution or dispersion may contain any of the conventional solvent or carrier systems for the compound, and may contain, for example, water, ethanol, polyol (for example, glycerol, propylene glycol and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. The prevention of the action of microorganisms can be brought about where necessary by the inclusion of various antibacterial and antifungal agents, for example, parabens, chlorobutanol, phenol, sorbic acid, thimerosal and the like. In many cases, it will be preferable to include agents to adjust osmolarity, for example, sugars or sodium chloride. Preferably, the formulation for injection will be isotonic with blood. Prolonged absorption of the intravenous compositions can be brought about by the use in the compositions of agents delaying absorption, for example, aluminium monostearate and gelatin.

Sterile intravenous solutions are prepared by incorporating the active compound in the required amount in the appropriate solvent with various of the other ingredients such as those mentioned above, as required, followed by filtered sterilization. Generally, dispersions are prepared by incorporating the various sterilised active ingredient into a sterile vehicle which contains the basic dispersion medium and the required other ingredients from those enumerated above. In the case of sterile powders for the preparation of sterile intravenous solutions, preferred methods of preparation are vacuum drying or freeze-drying of a previously sterile-filtered solution of the active ingredient plus any additional desired ingredients.

The oral formulations may be any type of solid oral dosage form, for example, tablets, minitablets or capsules. For example, the formulations of the invention may be compressed into tablet form or the coated particles may be filled into a capsule. Techniques for formulation of solid oral dosage forms are known in the art.

In a particular embodiment of the invention there is provided a formulation comprising a compound of formula (I) in a polymeric matrix, the polymeric matrix and compound of formula (I) mixture having a seal coating. The seal-coated polymeric matrix compound of formula (I) has a sustained-release coating and the formulation further comprises an enteric-release coating. Optionally, there is a buffer-coating between the sustained-release coating and the enteric-release coating.

In some embodiments, the compound of formula (I) is milrinone. In some embodiments, the polymer matrix of the core is HPMC or HPC (80,000 to 120,000) and HPMC (50 cps) in a ratio of 2:1 to 1:2, especially 1.5:1 to 1:1.5, more especially about 1:1. In some embodiments, the seal coating comprises a polymer selected from HMPC or PVA and a plasticiser selected from PEG and/or glycerine. In some embodiments, the buffer-coating comprises a polymer selected from HMPC or PVA and a plasticiser selected from PEG and/or glycerine. In some embodiments, the sustained-release coating comprises ethylcellulose. In some embodiments, the enteric-release coating comprises cellulose acetate phthalate polymers, hydroxypropyl methylcellulose phthalate polymers or copolymers of acrylic acids and their esters or methacrylic acid and their esters.

In some embodiments, the formulation may include or be administered with, sequentially and/or separately, other medications. Such medications include angiotensin converting enzyme (ACE) inhibitors such as, but not limited to, enalapril and ramipril; angiotensin receptor blockers such, as but not limited to, irbesartan and candesartan; calcium channel blockers such as, but not limited, to nifedipine and diltiazem; beta blockers such as, but not limited to, metoprolol and carvedilol; diuretics such as, but not limited to, frusemide, hydrochlorothiazide and spironolactone; and vasodilators such as, but not limited to, nitrates and hydralazine.

In order that the invention may be readily understood and put into practical effect, particular preferred embodiments will now be described by way of the following non-limiting examples.

EXAMPLES

Sustained release formulations of compounds of formula (I), and in particular sustained release formulations of milrinone, which achieve the desired release profile across the different environments encountered during transit through the GI tract in accordance with the invention are described in PCT application PCT/AU2012/000967, published as WO 2013/023250 A1. Examples of formulations that achieve the desired release profile are described below. The release profile of a sustained release formulation of a compound of formula (I) can be determined in accordance with the dissolution study methods described in WO 2013/023250 A1.

Example 1: Minitablet Formulation Comprising Hydroxypropylmethylcellulose Matrix Manufacturing Formula

| Ingredients | Mg/Tablet | For 700 g |
|---|---|---|
| Milrinone | 2.0 | 140.0 |
| HPMC K 100 | 3.0 | 210.0 |
| HPMC E50 | 3.0 | 210.0 |
| Avicel PH 102 Extragranular | 1.3 | 91.0 |
| Avicel PH 102 | 0.4 | 35.0 |
| Magnesium Stearate | 0.2 | 14.0 |
| Total | 10.0 | 700.0 |

Step 1: Weighing

All ingredients were weighed separately into a double polybag and/or butter paper.

Step 2: Sifting
1. HPMC 50 cps, Milrinone, HPMC K100M and Avicel PH102 were sifted through ASTM40 mesh.

Step 3: Granulation
1. Above sifted ingredients (intragranular) were added into rapid mixer granulator.
2. Dry mixing was done for 5 min. at impeller speed of 150 rpm.
3. 420 g Purified water was then added slowly in 2 minutes and wet massing was done for 2 minutes at 150 rpm with Chopper on at 1500 rpm.
4. Finally wet granules were unloaded from the bowl.

Step 4: Drying
1. Wet mass was dried in Rapid Dryer at product temperature of 50° C. for 45 min until % w/w moisture reduced to 3-4% w/w.
2. Granules were sifted through ASTM 30 mesh Step 5: Milling (Granules)
1. Granules were milled through screen no. 1016 (1 mm) using Co-mil
2. Step 4 and 5 granules were mixed together Step 6: Sifting
1. Extragranular Avicel is sifted through ASTM 40 mesh.
2. Magnesium stearate was sifted through ASTM 60 mesh.

Step 7: Blending (Extra-Granular)
1. Granules and Extragranular Avicel were mixed together into a double cone blender for 5 min at 15 rpm.
2. Granules and magnesium stearate were mixed together into a double cone blender for 15 min at 15 rpm.
3. Lubricated granules were unloaded into a double cone blender and were kept ready for compression.

Step 8: Compression
1. Cadmach CU 20 compression machine was fixed with one "D" tooling multitip punch set.
   a. Upper punch: 2 mm, round, standard concave (12 tips)
   b. Lower punch: 2 mm, round, standard concave (12 tips)

Step 9: In-Process Quality Control Testing of Core Minitablets

| In process parameters | Values/Observations | | |
|---|---|---|---|
| | Average | Minimum | Maximum |
| Hardness (N) | 20.5 | 15 | 25 |
| Thickness (mm) | 2.69 | 2.65 | 2.78 |
| Weight (mg) | 10.10 | 9.91 | 10.54 |

Step 10: Coating (Seal Coat)
1. Minitablets were seal coated using Opadry white at 10% w/w weight gain of film coat.
2. Coating was done using bottom spray container (2.4 liters) at following equipment parameters:

| Coating Process Parameter | Values |
|---|---|
| Inlet temperature | 45 to 55° C. |
| Product temperature | 38 to 42° C. |
| Exhaust temperature | 35 to 45° C. |
| Blower speed | 60 to 80% |
| Spray pump speed (rpm) | 5 to 15 |
| Atomization (Bars) | 0.9 to 1.2 |
| Air flow (cfm) | 65 to 94 |

Step 11: In-Process Quality Control Testing of Seal Coated Minitablets.

| In process parameters | Values/Observations | | |
|---|---|---|---|
| | Average | Minimum | Maximum |
| Hardness (N) | 28.5 | 25 | 37 |
| Thickness (mm) | 2.95 | 2.89 | 3.02 |
| Weight (mg) | 10.90 | 11.12 | 11.35 |

Step 12: Sustained Release Coating
1. 7.5% w/w sustained release coating of Minitablets was done using Aquacoat ECD 30 (Ethyl cellulose dispersion) where triethyl citrate was used as a plasticiser.

| Ingredients | Ratio to EC Solids | Total Dissolved Solids (TDS) (g) | Quantities Taken (g) |
|---|---|---|---|
| Aquacoat ECD (as 30% w/w suspension) | | 24.78 | 82.76 |
| Opadry Clear | 10% | 2.48 | 2.48 |
| Talc | 10% | 2.48 | 2.48 |
| Triethyl Citrate | 25% | 6.21 | 6.21 |
| Purified water | QS for 15% Solution | — | 146.02 |
| Total | | 36.00 | 239.95 |

2. Coating was done by Wurster coater (bottom spray container 2.4 liters) at following equipment parameters:

| Coating process parameter | Values |
|---|---|
| Inlet temperature | 50 to 60° C. |
| Product temperature | 38 to 42° C. |
| Exhaust temperature | 35 to 45° C. |
| Blower speed | 60 to 84% |
| Spray pump speed (rpm) | 5 to 15 |
| Atomization (Bars) | 0.9 to 1.2 |
| Air flow (cfm) | 65 to 95 |

3. After coating, curing was done for 2 hours at product temperature around 60° C. in Hot air oven.

Step 13: In-Process Quality Control Testing of Sustained Release Coated Minitablets

| In process parameters | Values/Observations | | |
|---|---|---|---|
| | Average | Minimum | Maximum |
| Hardness (N) | 37 | 30 | 45 |
| Thickness (mm) | 3.03 | 2.98 | 3.15 |
| Weight (mg) | 11.76 | 11.65 | 11.88 |

Step 14: Buffer Coating
1. Buffer coating was done at 5% w/w weight gain using Opadry white.
2. Coating was done using bottom spray container (2.4 liters) at following equipment parameters:

| Coating process parameter | Values |
|---|---|
| Inlet temperature | 45 to 55° C. |
| Product temperature | 38 to 42° C. |
| Exhaust temperature | 35 to 45° C. |
| Blower speed | 60 to 80% |
| Spray pump speed (rpm) | 5 to 15 |
| Atomization (Bars) | 0.9 to 1.2 |
| Air flow (cfm) | 65 to 94 |

Step 15: Enteric Coating
1. Enteric coating of buffer coated minitablets was done by using Eudragit L30 D55 polymer at 30% w/w weight gain where talc was used as an anti-tacking agent and triethyl citrate was used as a plasticiser.

| Ingredients | Ratio to Eudragit Solids | TDS (g) | Quantities Taken (g) |
|---|---|---|---|
| Eudragit 130 D55 | | 90.00 | 300.00 |
| Talc | 50 | 45.00 | 45.00 |
| Triethyl Citrate | 10 | 9.00 | 9.00 |
| Purified water | QS for 20% Solution | — | 366.00 |
| Total | | 144.0 | |

2. Coating was done using bottom spray container (2.4 L) at following equipment parameters,

| Coating process parameter | Values |
|---|---|
| Inlet temperature | 28 to 34° C. |
| Product temperature | 25 to 30° C. |
| Exhaust temperature | 28 to 32° C. |
| Blower speed | 50 to 98% |
| Spray pump speed (rpm) | 5 to 14 |
| Atomization (Bars) | 0.8 to 1.3 |
| Air flow (cfm) | 60 to 100 |

3. After coating curing of Minitablets was done for 2 hour at product temperature 40° C. in hot air oven.

Step 16: In-Process Quality Control Testing of Enteric Coated Minitablets

| In process parameters | Values/Observations | | |
|---|---|---|---|
| | Average | Minimum | Maximum |
| Hardness (N) | 54.5 | 42 | 67 |
| Thickness (mm) | 3.23 | 3.18 | 3.26 |
| Weight (mg) | 16.10 | 15.80 | 16.45 |

Example 2: Minitablet Formulation Comprising Hydrophilic Matrix of Natural Gums

| Ingredients | Quantity of Materials (g) |
|---|---|
| Milrinone | 50.25 |
| Xanthan gum | 37.50 |
| Locust gum | 37.50 |
| Avicel PH102 | 49.75 |
| Lactose, Anhydrous | 62.50 |
| PVPK30 | 8.75 |
| Aerosil | 2.50 |
| Magnesium stearate | 1.25 |
| Total | 250.0 |

Step 1: Dispensing

All the ingredients were weighed separately into double polybags. Milrinone quantity was weighed based upon following calculation:

Assay of Milrinone=99.70% (as is basis).

Mg/tablet of Milrinone=Theoretical quantity of Milrinone (mg/tablet)×100/Assay of Milrinone=2.00×100/99.7=2.01 mg The quantity of API (active pharmaceutical ingredient) was adjusted with microcrystalline cellulose.

Step 2: Sifting
1. All the ingredients except magnesium stearate were sifted through ASTM 40 mesh.
2. Magnesium stearate was sifted through ASTM 60 mesh.

Step 3: Blending
1. Ingredients 1 to 3 from above Table were transferred into a 0.5 L Turbula Shaker Mixer container and blending was done for 10 min at 49 rpm.
2. Ingredients 4 to 7 were then added and further blending was done for 10 min at 49 rpm.
3. Ingredient 8 was then added and lubrication was done for 5 min at 49 rpm.
4. Blend was finally collected into a double polybag.

Step 4: Compression
1 Cadmach CU 20 compression machine was fixed with one "D" tooling multitip punch set.
   a. Upper punch: 2 mm, round, standard concave (12 tips)
   b. Lower punch: 2 mm, round, standard concave (12 tips)
2. Tablets were compressed using Cadmach CU 20 compression machine. Compression was done manually by rotating hand wheel to obtain enough hardness and thickness.

Step 5: In-Process Quality Control Testing of Core Minitablets

| In process parameters | Values/Observations | | |
|---|---|---|---|
| | Average | Minimum | Maximum |
| Hardness (N) | 28 | 23 | 35 |
| Thickness (mm) | 2.47 | 2.42 | 2.53 |
| Weight (mg) | 10 | 9.0 | 10.0 |
| Friability | | Nil | |

Step 5: Seal Coating
1. Seal coating of minitablets was done at 3% w/w weight gain using Opadry white as a film coating agent. Opadry film coating system powder was added to water and mixed for 45 minutes with a propeller stirrer. The coating suspension can be made according to the manufacturer's instructions.
2. Coating was done by using Gansons coater (GAC-275) at the following parameters:

| Coating process parameter | Values |
|---|---|
| Inlet temperature | 60 to 62.3° C. |
| Product temperature | 38 to 40° C. |
| Exhaust temperature | 39 to 40° C. |
| Spray pump speed (rpm) | 2 to 3 |
| Atomization air (kg/cm$^2$) | 0.2 |
| Fan pressure (kg/cm$^2$) | 0.2 |

Step 6: In-Process Quality Control Testing of Seal Coated Minitablets

| In process parameters | Values/Observations | | |
|---|---|---|---|
| | Average | Minimum | Maximum |
| Hardness (N) | 32 | 29 | 38 |
| Thickness (mm) | 2.52 | 2.50 | 2.55 |
| Weight (mg) | 10.3 | 10.1 | 10.5 |
| Friability | | Nil | |

Step 7: Sustained Release (SR) Coating of Minitablets
1. Minitablets were 5% w/w SR coated by ethylcellulose dispersion (Aquacoat ECD30D) using triethyl citrate as a plasticiser.

| Ingredients | Quantities (g) |
|---|---|
| Aquacoat ECD30D | 140.28 g |
| Triethyl citrate | 8.42 g |

2. Coating was done by using Gansons coater (GAC-275) at the following parameters:

| Coating process parameter | Values |
|---|---|
| Inlet temperature | 56 to 59° C. |
| Product temperature | 38 to 40° C. |
| Exhaust temperature | 39 to 40° C. |
| Spray pump speed (rpm) | 2 to 2.5 |
| Atomization air (kg/cm$^2$) | 0.2 |
| Fan pressure (kg/cm$^2$) | 0.2 |

3. Curing of minitablets was done at 60° C. for 2 hours in vacuum oven (without vacuum).

Step 8: In-Process Quality Control Testing of SR Coated Minitablets

| In process | Values/Observations | | |
|---|---|---|---|
| parameters | Average | Minimum | Maximum |
| Hardness (N) | 37.4 | 34 | 41 |
| Thickness (mm) | 2.65 | 2.61 | 2.68 |
| Weight (mg) | 10.62 | 10.2 | 10.9 |

Step 9: Buffer Coating
1. Seal coating of minitablets was done at 5% w/w weight gain using Opadry white as a film coating agent, as described in step 5 of Batch-028.
2. Coating was done by Wurster coater 2.4 L container (GPCG 1.1) at the following parameters:

| Coating process parameter | Values |
|---|---|
| Inlet temperature | 58 to 60.3° C. |
| Product temperature | 39 to 40° C. |
| Exhaust temperature | 39 to 40° C. |
| Spray pump speed (rpm) | 2 to 4 |
| Atomization air (kg/cm$^2$) | 0.2 |
| Fan pressure (kg/cm$^2$) | 0.2 |

Step 10: In-Process Quality Control Testing of Buffer Coated Minitablets

| In process | Values/Observations | | |
|---|---|---|---|
| parameters | Average | Minimum | Maximum |
| Hardness (N) | 41.7 | 37 | 46 |
| Thickness (mm) | 2.74 | 2.70 | 2.78 |
| Weight (mg) | 11.15 | 11.03 | 11.23 |

Step 11: Enteric Coating
1. Enteric coating of buffer coated minitablets was done by Eudragit L30D55 as a enteric polymer along with triethylcitrate as a plasticiser and talc as an anti-tacking agent.

| Ingredients | Quantities (g) |
|---|---|
| Eudragit L30D55 | 333.33 g |
| Triethyl citrate | 10.00 g |
| Talc | 50.00 g |

2. Coating was done by Wurster coater 2.4 L container (GPCG 1.1) at the following parameters, to provide an enteric coat of 40% w/w.

| Coating process parameter | Values |
|---|---|
| Inlet temperature | 27 to 32° C. |
| Product temperature | 26 to 28° C. |
| Exhaust temperature | 26 to 28° C. |
| Blower speed (%) | 58 to 92 |
| Air flow (cfm) | 70 to 134 |
| Spray pump speed (rpm) | 2 to 3 |
| Atomization air (Bars) | 1.0 to 1.2 |

Step 12: In-Process Quality Control Testing of Enteric Coated Minitablets

| In process | Values/Observations | | |
|---|---|---|---|
| parameters | Average | Minimum | Maximum |
| Hardness (N) | 89.89 | 74 | 107 |
| Thickness (mm) | 3.08 | 3.03 | 3.14 |
| Weight (mg) | 15.61 | 15.58 | 15.65 |

Example 3: Formulation of Milrinone Beads

| Sr. No. | Name of equipment/instrument | Manufacturer/supplier |
|---|---|---|
| 01 | Weighing balance | Sartorius |
| 02 | Sieves | Lab Supplies India Pvt. Ltd. |
| 03 | Propeller Mixer | Hally Instruments |
| 04 | Wurster coater 2.4 L (GPCG 1.1) | Glatt |
| 05 | Homogenizer | Silversons |
| 06 | Vacuum oven | Servewell Instruments |

| Ingredients | Manufacturer | % of Solids | Quantities (g) |
|---|---|---|---|
| Milrinone | Chemzam Pharmatech | 61 | 45.00 |
| Kollidon 30 (binder) | BASF | 6 | 4.50 |
| Opadry white | Colorcon | 33 | 24.50 |
| Purified water | FDC In-house | | 495.23 |

Step 1: Drug Layering
1. Procedure for drug dispersion preparation:
   a. Milrinone, Kollidon 30 and Opadry white were sifted through ASTM 30 mesh. All ingredients were collected into a single polybag.
   b. Purified water was weighed into a beaker and was placed under propeller mixer to create vigorous vortex.
   c. Slowly ingredients from step a. were added into water maintaining vortex. After complete addition, propeller mixer speed was reduced to avoid vortex. Mixing was done for 30 min.
2. Drug layering by Wurster coater
   a. Wurster coater was equipped with following accessories,
      i) 2.4 L bottom spray container
      ii) Wurster column at 20 mm height
      iii) 1.2 mm liquid nozzle insert
   b. 350.0 g of sugar spheres (30/35 #) [Werner, Germany] were transferred into the container.
   c. Sugar spheres were warmed to reach product temperature of 40° C.
   d. Drug dispersion was sprayed on sugar spheres at following parameters recorded over the period of 255 min coating time:

| Coating process parameter | Values |
|---|---|
| Inlet temperature | 45 to 50° C. |
| Product temperature | 39 to 42° C. |
| Exhaust temperature | 36 to 41° C. |
| Blower speed (%) | 60 to 77% |

| Coating process parameter | Values |
|---|---|
| Spray pump speed (rpm) | 2 to 6 |
| Atomization air (Bars) | 0.8 to 1.2 |
| Air flow (cfm) | 73 to 92 | e. After coating, peristaltic pump was stopped and product temperature was allowed to reach 44° C. and then coating process was stopped.

f. Total yield was 390.43 g.

There are two methods of determining % w/w weight gain during spray coating of beads.

Method A:

Weight gain can be calculated only after complete coating process and then the following formula can be applied to find out weight gain:

% w/w practical weight gain achieved=Final weight−Initial weight/Initial weight×100

Method B:

Coating dispersion/solution shall be prepared exactly as per described except. 40% w/w for enteric coating with 10% extra solution to cover the in-process losses. Since the solution quantity equivalent to 40% w/w is sprayed completely on the beads, it is considered that final weight gain achieved is 40% w/w.

Step 2: Seal Coating of Drug Layered Beads (10% w/w)

1. GPCG1.1 was equipped with following accessories,
   a. 2.4 L bottom spray container
   b. Wurster column at 20 mm height
   c. 1.2 mm liquid nozzle insert
2. Preparation of coating solution

| Ingredients | Manufacturer | Quantities (g) |
|---|---|---|
| Opadry white | Colorcon | 42.9 |
| Purified water | FDC in-house | 493.35 | a. A vigorous vortex was created into a weighed quantity of water and slowly Opadry white was added into it. After complete addition, speed was reduced to avoid vortex. Mixing was done for 45 min.

b. Coating solution was sprayed on 390.0 g of drug layered spheres at following parameters recorded over the period of 260 min. of coating time:

| Coating process parameter | Set Values | Actual Values |
|---|---|---|
| Inlet temperature | 47 ± 5° C. | 44 to 51° C. |
| Product temperature | 40 ± 3° C. | 39 to 42° C. |
| Exhaust temperature | 40 ± 3° C. | 39 to 41° C. |
| Blower speed | 57 to 70% | 57 to 70% |
| Spray pump speed (rpm) | 2 to 7 | 2 to 7 |
| Atomization (Bars) | 0.8 to 1.4 | 0.8 to 1.4 |
| Air flow (cfm) | N/A | 73 to 92 |

Note: Before starting coating, beads were warmed to reach 40° C. product temperature.

c. After coating, temperature was allowed to reach 45° C. and then coating process was stopped.

Total yield was found to be 412.0 g.

Step 3A: First Layer Sustained Release (SR) Coating of Seal Coated Beads (Using Eudragit RS30D and Eudragit RL30D at 9:1 Ratio) to Prepare Beads with 10% w/w Coating.

1. Preparation of coating dispersion:

| Ingredients | Manufacturer | Ratio to total Eudragit solids (%) | TDS (g) | Quantities (g) |
|---|---|---|---|---|
| Eudragit RS30D | Evonik | 90 | 22.91 | 76.37 |
| Eudragit ROOD | Evonik | 10 | 2.55 | 8.50 |
| Talc | Luzenac Pharma | 50 | 12.72 | 12.72 |
| Triethylcitrate | Sigma-Aldrich | 20 | 5.09 | 5.09 |
| Purified water | FDC In-house | | | 272.32 |
| Total | | | | 375.00 | a. Eudragit RL30D and Eudragit RS30D were mixed together into a beaker.

b. Talc and triethylcitrate were homogenized for 10 min. at 4500 rpm in purified water at 4500 rpm of Homogenizer.

c. Polymer dispersion from step a. was then added into b. excipient dispersion and mixing was done for 30 min. at 380 rpm using propeller mixer.

2. 412.0 g of beads were transferred into the 2.4 L bottom spray container of GPCG1.1 and warmed to reach 28° C.

3. Coating was done on beads at the following parameters recorded over the period of 303 min. of coating process to achieve a first layer SR coating of 10% w/w.

| Coating process parameter | Values |
|---|---|
| Inlet temperature | 27 to 31° C. |
| Product temperature | 25 to 27° C. |
| Exhaust temperature | 25 to 27° C. |
| Blower speed | 58 to 71% |
| Spray pump speed (rpm) | 2 to 3 |
| Atomization (Bars) | 0.8 to 1.0 |
| Air flow (cfm) | 71 to 98 |

4. Total yield was 451.0 g. 21.00 g of beads were cured at 50° C. for 30 minutes in vacuum oven without vacuum for analysis (dissolution test).

Step 3B: First Layer Sustained Release (SR) Coating of Seal Coated Beads (Using Eudragit RS30D and Eudragit RL30D at 9:1 Ratio) to Prepare Beads with 15% w/w Coating.

Beads prepared according to Step 2 were coated with Sustained Release coating dispersion of Eudragit RS30D and Eudragit ROOD at 9:1 ratio described in Step 3A according to the procedures described therein but for sufficient duration to achieve a Sustained Release coating of 15% w/w on beads.

Step 3C: First Layer Sustained Release (SR) Coating of Seal Coated Beads (Using Eudragit RS30D and Eudragit RL30D at 9:1 Ratio) to Prepare Beads with 20% w/w Coating.

Beads prepared according to Step 2 were coated with Sustained Release coating dispersion of Eudragit RS30D and Eudragit ROOD at 9:1 ratio described in Step 3A according to the procedures described therein but for sufficient duration to achieve a Sustained Release coating of 20% w/w on beads.

Step 3D: First Layer Sustained Release (SR) Coating of Seal Coated Beads (Using Eudragit RS30D and Eudragit RL30D at 9:1 Ratio) to Prepare Beads with 25% w/w Coating.

Beads prepared according to Step 2 were coated with Sustained Release coating dispersion of Eudragit RS30D and Eudragit ROOD at 9:1 ratio described in Step 3A according to the procedures described therein but for sufficient duration to achieve a Sustained Release coating of 25% w/w on beads.

Step 3E: Second Layer Sustained Release (SR) Coating of First Layer SR Beads Using Eudragit RS30D to Prepare Beads with Total SR 30% w/w Coating 1. Preparation of coating dispersion:

| Ingredients | Manufacturer | Quantities (g) |
|---|---|---|
| Eudragit RS30D | Evonik | 84.87 |
| Talc | Luzenac Pharma | 12.72 |
| Triethylcitrate | Sigma-Aldrich | 5.09 |
| Purified water | FDC In-house | 169.64 | a. Eudragit RS30D was added to a beaker.
b. Talc and triethylcitrate were homogenised for 10 min. at 4500 rpm in purified water at 4500 rpm of Homogeniser.
c. Polymer from step a. was then added into b. excipient dispersion and mixing was done for 30 min. at 380 rpm using propeller mixer.

2. Single Layer SR beads from Step 3D were transferred into the 2.4 L bottom spray container of GPCG 1.1 and warmed to reach 28° C.
3. Coating was done on beads at the following parameters recorded over a sufficient period of coating process to achieve a second layer SR coating of 5% w/w and a total SR coating of 30%.

| Coating process parameter | Values |
|---|---|
| Inlet temperature | 27 to 31° C. |
| Product temperature | 25 to 27° C. |
| Exhaust temperature | 25 to 27° C. |
| Blower speed | 58 to 71% |
| Spray pump speed (rpm) | 2 to 3 |
| Atomization (Bars) | 0.8 to 1.0 |
| Air flow (cfm) | 71 to 98 |

4. Total yield of beads were cured at 50° C. for 30 min. in vacuum oven without vacuum for analysis (dissolution test).

Step 3F: Second Layer Sustained Release (SR) Coating of First Layer SR Beads Using Eudragit RS30D to Prepare Beads with Total SR 40% w/w Coating Beads prepared according to Step 3D were coated with Sustained Release coating dispersion of Eudragit RS30D described in Step 3E according to the procedures described therein but for sufficient duration to achieve a second layer Sustained Release coating of 15% w/w and a total SR coating of 40% w/w.

Step 4: Buffer Coating of SR Coated Beads (at 10% w/w Weight Gain with Opadry White)

1. Preparation of coating solution

| Ingredients | Manufacturer | Quantities (g) |
|---|---|---|
| Opadry white | Colorcon | 43.44 |
| Purified water | FDC in-house | 680.56 |

Preparation procedure was same as that of step 2 (2) above.

2. Coating was done on beads using GPCG1.1 bottom spray assembly at the following parameters recorded over the period of 180 min. of coating process.

| Coating process parameter | Values |
|---|---|
| Inlet temperature | 43 to 52° C. |
| Product temperature | 39 to 43° C. |
| Exhaust temperature | 35 to 43° C. |
| Blower speed | 63 to 72% |
| Spray pump speed (rpm) | 2 to 4 |
| Atomization (Bars) | 1.0 to 1.2 |
| Air flow (cfm) | 72 to 91 |

Step 5: Enteric Coating with Eudragit L30D55 at 40% w/w Enteric Weight Gain

1. Coating solution preparation

| Ingredients | Manufacturer | Quantities (g) |
|---|---|---|
| Eudragit L30D55 | Evonik | 395.00 |
| Talc | Luzenac Pharma | 11.85 |
| Triethylcitrate | Sigma-Aldrich | 59.25 |
| Purified water | FDC Inhouse | 797.90 |

Note: Above solution was based on 395.00 g of pan load for coating and 20% extra quantities considering losses.

2. Talc and triethylcitrate were homogenised in water for 10 min. Then this excipient dispersion was poured slowly into Eudragit L30D55 dispersion while stirring slowly at 250 rpm. Finally speed was reduced to 200 rpm and mixing was done for 30 min.
3. Initially, beads were warmed to reach product temperature of 28° C. and then coating was started which lasted for 765 min and the parameters recorded are given below,

| Coating process parameter | Values |
|---|---|
| Inlet temperature | 28 to 32° C. |
| Product temperature | 26 to 28° C. |
| Exhaust temperature | 26 to 29° C. |
| Blower speed | 63 to 75% |
| Spray pump speed (rpm) | 2 to 7 |
| Atomization (Bars) | 1.2 to 1.5 |
| Air flow (cfm) | 69 to 96 |

3. Finally, curing was done for 2 hours between 40 to 43° C. in the equipment. Total yield was 543.00 g at the end of the process.

Example 4: Immediate Release Milrinone Formulation

| Sr. No. | Composition | % w/w | Amount/tablet (mg) |
|---|---|---|---|
| 01 | Milrinone | 20 | 02 |
| 02 | Avicel PH 102 | 30 | 03 |
| 03 | Lactose anhydrous | 45 | 4.5 |
| 04 | Kollidon 30 | 3.5 | 0.35 |
| 05 | Aerosil | 01 | 0.1 |
| 06 | Magnesium stearate | 0.5 | 0.05 |
| | Total | 100 | 10.0 |

Procedure:
1. Weighing:
   All the listed ingredients were accurately weighed into double line polybags, labelled and tagged.
2. Sifting:
   All the excipients and Milrinone except magnesium stearate were sifted through ASTM 40 mesh.
   Magnesium stearate is sifted through ASTM 60 mesh.
3. Blending:
   Milrinone and other excipients except magnesium stearate were added into Turbula shaker mixer and mixed for 15 min. Magnesium stearate was added into the blend and mixed for 5 min.
4. Compression:
   The lubricated blend was compressed using circular B tooling punches with 2 mm tips.

In Process Checks:
Weight of Tablets: 10 mg
Hardness: 30 N-40 N
Thickness: 2.4 mm-2.5 mm
Friability: 0.486%
Disintegration test: 4 to 5 min.

Example 5: pH Solubility Studies on Milrinone

Aim: To perform the saturated solubility of Milrinone in different buffers.
Buffers:
1. pH 1.2—Hydrochloric Acid Buffer
2. pH 4.5—Acetate Buffer
3. pH 6.8—Phosphate Buffer
4. pH 7.4—Phosphate Buffer.

Procedure:
1. 2 mL buffer solution is placed into a 8 mL USP Type I clear glass vial (with screw cap and PTFE septa)
2. 10 mg of Milrinone is added in each vial and the vial is shaken to dissolve the compound.
3. The addition of Milrinone is continued till the formation of saturated solution.
4. The pH of the saturated solution is measured after the addition of Milrinone.
5. If there is any difference in pH more than 0.1 units is observed when compared to the initial pH, the pH was adjusted with acid or base respectively to bring it to the initial pH.
6. The vials are closed with screw cap and kept for mixing using rotary tube shaker for 24 h.

Note: The vials are observed at frequent intervals and if the solution is clear, further amount of Milrinone is added to make a saturated solution.

Results:
The solubility of Milrinone at different pH buffers

| Sr. No. | Buffer | Saturated solubility (mg/mL) |
|---|---|---|
| 1 | pH 1.2 Hydrochloric Acid Buffer | 25.385 mg/mL |
| 2 | pH 4.5 Acetate Buffer | 1.826 mg/mL |
| 3 | pH 6.8 Phosphate Buffer | 0.742 mg/mL |
| 4 | pH 7.4 Phosphate Buffer | 0.603 mg/mL |

Conclusion

The solubility results indicate that Milrinone is highly soluble in acidic pH, and the solubility is decreased gradually with increase in pH. Thus the discriminatory dissolution media for Milrinone tablets should be pH 6.8 or 7.4.

Example 6: Dissolution Profiles of Formulations

The following procedure was used to determine if a sustained release formulation of a compound of formula (I) would achieve the desired release profile across the different environments encountered during transit through the GI tract. The desired sustained-release formulation provides zero order kinetics of drug delivery (i.e. a linear delivery with respect to time). Controlled release of drug from the dosage form relies upon two processes: dissolution and release.

Reagents
1. Potassium dihydrogen orthophosphate (AR grade)
2. Hydrochloric acid (AR grade)
3. Sodium hydroxide (AR grade)
4. Methanol (HPLC grade)
5. Water (HPLC grade)

Dissolution Parameters (for Acid Stage)
Medium: 0.1N Hydrochloric acid, 900 mL
Temperature: 37.0±0.5° C.
Apparatus: USP Apparatus II (paddle)
Rotational speed: 50 rpm
Sampling time: 2 h Preparation of 0.1N Hydrochloric Acid pH 1 Diluent and Dissolution Buffer
8.5 mL of concentrated hydrochloric acid in 1000 mL of water, mix well.

Preparation of pH 6.8 Diluent
Dissolve 6.8 g Potassium dihydrogen orthophosphate and 0.9 g of sodium hydroxide in 1000 mL of water and adjust the pH to 6.8 with sodium hydroxide solution or orthophosphoric acid.

Preparation of Standard Solution for pH 1 Analysis of Milrinone
Accurately weigh and transfer about 55 mg of Milrinone working standard into a 100 mL volumetric flask. Add about 10 mL of methanol and sonicate to dissolve then make up to the mark with 0.1N hydrochloric acid. Dilute 5 mL of above solution to 100 mL with 0.1N hydrochloric acid. Further dilute 5 mL of above solution to 100 mL with 0.1N HCl.

Preparation of Sample Solution
Transfer the content of one capsule in each of the six dissolution vessels and start the dissolution test in 0.1N HCl Dissolution Buffer. At the specified time withdraw about 10 mL of the aliquot from each dissolution vessel. Further dilute 4 mL of above solution to 10 mL with 0.1N HCl Diluent.

Dissolution Parameters (for 0.1N HCl Buffer Stage)
Medium: 0.1N Hydrochloric acid, 900 mL
Temperature 37.0±0.5° C.
Apparatus USP Apparatus II (paddle)

Rotational speed 50 rpm
Sampling time 1 h, 2 h
Where test article is to be exposed to 0.1N HCl Dissolution Buffer for 2 hours and then exposed to pH 6.8 Buffer for 12 hours, the test article is removed from the dissolution vessel, washed briefly with water and placed immediately into the required dissolution vessel containing the pH 6.8 Buffer.

Procedure

Measure the absorbance of standard (in duplicate) and sample solution using dissolution medium as blank at 265 nm.

Calculation $$\% \text{ of drug released} = \frac{AT}{AS} \times \frac{DS}{DT} \times \frac{P}{100} \times \frac{100}{C}$$

Wherein:
AT=Absorbance of sample solution.
AS=Average absorbance of standard solution.
DS=Dilution factor of the standard solution.
DT=Dilution factor of the sample solution.
P=Percent potency of Milrinone working standard, on as is basis.
C=Label claim of Milrinone per capsule (in mg).

Dissolution Parameters (for Buffer Stage)
  Medium pH 6.8 Buffer, 900 mL
  Temperature 37.0±0.5° C.
  Apparatus USP Apparatus II (paddle)
  Rotational speed 50 rpm
  Sampling time 1 h, 2 h, 3 h, 4 h, 5 h, 6 h, 7 h, 8 h, 9 h, 10 h, 11 h, and 12 h Preparation of pH 6.8 Dissolution Buffer and Diluent.

Dissolve 6.8 g Potassium dihydrogen orthophosphate and 0.9 g of sodium hydroxide in 1000 mL of water and adjust the pH to 6.8 with sodium hydroxide solution or orthophosphoric acid.

Preparation of Standard Solution

Accurately weigh and transfer about 55 mg of Milrinone working standard into a 100 mL volumetric flask. Add about 10 mL of methanol and sonicate to dissolve, then make up to the mark with pH 6.8 Diluent. Dilute 5 mL of above solution to 200 mL with Diluent.

Preparation of Sample Solution

Transfer the content of one capsule in each of the six dissolution vessels and start the dissolution test in pH 6.8 Dissolution Buffer. At the specified time withdraw about 10 mL of the aliquot from each dissolution vessel. Further dilute 4 mL of above solution to 10 mL with diluent.

Procedure

Measure the absorbance of standard (in duplicate) and sample solution using dissolution medium as blank at 265 nm.

Calculation $$\% \text{ of drug released} = \frac{AT}{AS} \times \frac{DS}{DT} \times \frac{P}{100} \times \frac{100}{C}$$

Wherein:
AT=Absorbance of sample solution.
AS=Average absorbance of standard solution.
DS=Dilution factor of the standard solution.
DT=Dilution factor of the sample solution.
P=Percent potency of Milrinone working standard, on as is basis.
C=Label claim of Milrinone per capsule (in mg).

Example 6

TABLE 1

Dissolution Profile Of Enteric Coated Minitablet Of Example 1 In 0.1n HCl Followed By pH 6.8 Phosphate Buffer

| Time | Example 1 (30% Enteric Coat) |
|---|---|
| 0 | 0 |
| 1 | 0 |
| 2 | 0 |
| 3 | 8 |
| 4 | 19 |
| 5 | 29 |
| 6 | 42 |
| 7 | 55 |
| 8 | 67 |
| 9 | 76 |
| 10 | 85 |
| 11 | 93 |
| 12 | 97 |
| 13 | 102 |
| 14 | 104 |
| $R^2$ value | 0.974 |
| Assay | 105.4% w/w |

Conclusion

The formulation of Example 1 showed zero order release profile and showed maximum release up to 105% (the assay of this batch is 105%). The enteric coating of 30% was sufficient to prevent the drug release in stomach.

This dissolution profile data demonstrates the in vitro zero order release of Milrinone from a formulation of the invention over 12 hours, and a sustained release profile which is consistent with intravenously administered Milrinone. In particular, dissolution profiles show zero order release of Milrinone at pH 6.8 over about 12 hours (i.e. R2>0.9) to provide about 100% release of the active pharmaceutical ingredient. This sustained release profile is consistent with providing a plasma exposure in patients that is similar to that achieved by a dosing regime with intravenous formulations of Milrinone Example 7: Pharmacokinetic Study of HPMC ER Milrinone Formulation (Example 1) Versus IR Milrinone Formulation (Example 4) in Dogs Experimental Materials Pentagastrin and Ammonium formate were purchased from Sigma (St. Louis, Mo.). Amrinone was purchased from LKT Lab (St. Paul, Minn.). Milrinone formulations Example 1 (ER milrinone) and Example 4 (IR milrinone) were prepared as described. Gelatin capsules were received from Torpac (Fairfield, N.J.). Dichloromethane and high performance liquid chromatography (HPLC) grade acetonitrile was purchased from Honeywell (Muskegon, Mich.). Water was obtained using a Millipore system (Billerica, Mass.). American Chemical Society grade formic acid was received from Acros Organics (New Jersey).

Animals

Purpose-bred female beagle dogs (Marshall Farms, North Rose, N.Y.) weighing between 8 and 11 kg were housed unrestrained in accordance with Association for Assessment and Accreditation of Laboratory Animal Care International (AAALAC) guidelines.

Dogs were maintained on 300 g of 21% protein dog diet #2021 (Harlan Teklad, Madison, Wis.) once daily when not on study. Prior to each study, dogs were fasted overnight. All studies were conducted in accordance with the Guide for the Care and Use of Laboratory Animals (National Research Council, 1996).

Gastric pH-Modifying Treatment and Dosing

Pentagastrin was dissolved in saline (0.024 mL/kg) and administered via FM injection in the animal's right or left hind leg (6 ug/kg) 30 minutes prior to test article administration. Following dose administration, the area was gently massaged.

The oral milrinone doses were prepared by counting minitablets into size-3 gelatin capsules. One or two milrinone filled capsule was orally administered to each dog, followed by water (10 mL) to assist swallowing. The experiments were conducted in two groups of three dogs each.

Assessing pH-Dependent Absorption

Beagle dogs (n=3) were dosed in a nonrandomized, crossover design, with at least a 1 week washout between treatments. All animals were fed their normal daily ration of food the day prior to dose administration. All animals were fasted at 17:40 the day prior to IR dose administration and at 18:22 the day prior to ER dose administration. All animals were fed following the 3 hr collections. The IR and ER milrinone formulations were orally administered (5 mg/kg in gelatin capsules) to pentagastrin-pretreated animals. Serial blood samples (2 mL) were collected from the jugular vein into potassium ethylenediaminetetraacetic acid tubes before dose and 0.5, 1, 1.5, 3, 6, 9, 11, 12, 14, 18, 24, 30, 36, 42 and 48 h after dose. Blood samples were kept on ice until processed for plasma. Blood samples were centrifuged at 3200 RPM for 10 minutes at approximately 5° C. Plasma samples were directly transferred to 96-well plate tubes (1.1 mL). Plugs were placed on the tubes. Plasma samples were stored at −20±5° C. until analyzed by liquid chromatography tandem mass spectrometry (LC/MS/MS).

Sample Analysis

Milrinone was extracted from dog plasma using dichloromethane protein precipitation. Calibration curves were constructed using commercial beagle dog plasma spiked with individual test compounds over the analysis range of 0.5-500 ng/mL. Fifty microliters of each plasma sample and internal standard (amrinone, 2 ng) were added to micro centrifuge tubes. One volume (1.0 mL) of dichloromethane was added to each tube, and the rack was vortexed for approximately 6 min to aid in the precipitation. The tubes were centrifuged at 13,000 rpm at room temperature for 6 min. Supernatants (800 uL) were transferred to a clean culture tubes and dried down at room temperature using Turbovap. The recon solution (150 uL of mobile phase A) was added to the dried tubes and subjected to LC/MS/MS analysis. Sample analysis was performed with 20 uL sample injection on an AB Sciex API-4000 triple quadrupole mass spectrometer. Analytes were separated using a Betasil C8 (100×2.1 mm) 5 m (Thermo Electron Co).

Chromatographic conditions were 10% mobile phase A (1/9, acetonitrile/10 mM ammonium formate, pH 3.0) and 90% mobile phase B (0.1% formic acid in acetonitrile) at 0.3 ml/min, ramped to 80% MP A in 1.5 min, then to 90% MP-A in 2 min. The system was returned to initial over 10 sees, and the column was reequilibrated at initial conditions for 1.4 min. LC/MS/MS analysis was carried out at positive ion mode using multiple reaction monitoring (MRM) transitions for milrinone (m/z 212→140) and the internal standard (amrinone, m/z 188→133). Data analysis used linear fitting with $1/x^2$ weighting. All analytical results were within acceptable specifications, including performance of quality control samples, reproducibility, linearity, accuracy, and precision. The lower limit of quantitation was established at 0.5 ng/mL using the predefined criteria for reproducibility, accuracy, and precision.

Pharmacokinetic Analysis

The plasma concentrations versus time profiles obtained after oral administration of IR Milrinone and ER Milrinone were analyzed using noncompartmental analysis (WinNonlin Professional, Version 5.2 software; Pharsight Corp., Mountain View, Calif.). $C_{max}$ was defined as the highest observed plasma concentration, and $J_{max}$ was the time at which $C_{max}$ occurred. The area under the concentration-time curve from zero to the last quantifiable time point (AUCO-t) was calculated using the Linear Up/Log Down method. AUCO-t was extrapolated to infinity and reported as AUCO-co.

RESULTS

Effect of Different Treatments on Gastric pH

Table 1 provides the pharmacokinetic values for the IR Milrinone and ER Milrinone formulation dosing in groups of 3 dogs. This data shows that the ER Milrinone achieved a reduced Cmax in comparison to the IR Milrinone (650 ng/mL vs 3180 ng/mL); that the ER Milrinone a similar overall exposure as measured by the AUC in comparison to the IR Milrinone (6751 ng*hr/mL vs 9478 ng*hr/mL), and that the ER Milrinone maintained stable milrinone plasma concentrations over a 12 hour period.

Example 7

TABLE 1

Summary Pharmacokinetic Parameters of Milrinone In The Plasma Of Female Beagle Dogs Following 5 Mg/Kg Po Administration Of Immediate Or Extended Release Tablets In A Gelatin Capsule

| Parameter (units) | Group 1 (Immediate Release) | | Group 2 (Extended Release) | |
|---|---|---|---|---|
| | Mean | SD | Mean | SD |
| $C_{max}$ (ng/mL) | 3180 | 1173 | 650 | 113 |
| $t_{max}$ (hr) | 1.00 | 0.50 | 7.67 | 4.16 |
| $AUC_{(0-t)}$ (ng · hr/mL) | 9478 | 3695 | 6751 | 2150 |
| $AUC_{(0-\infty)}$ (ng · hr/mL) | 9488 | 3696 | 6759 | 2152 |
| $t_{1/2}$(hr) | 4.97 | 0.77 | 3.71 | 0.83 |
| Vz_obs (mL/hr/kg) | 4029 | 965 | 4143 | 1049 |
| Cl_obs (mL/hr/kg) | 586 | 234 | 802 | 298 |

| PK Parameter Descriptions | |
|---|---|
| $C_{max}$: | Maximum Observed Concentration |
| $t_{max}$: | Time Point at $C_{max}$ |
| $AUC_{(0-t)}$: | AUC to the last non-zero concentration (t is the corresponding time) |
| $AUC_{(0-\infty)}$: | $AUC_{(0-\infty)} = AUC_{(0-t)} + AUC_{(0-\infty)}$ |
| $t_{1/2}$: | Half-life; time taken for drug plasma concentration to fall by one- half, |
| Vz_obs: | Observed Volume of Distribution |
| Cl_obs: | Observed Clearance |

Example 7

TABLE 2

Individual Female Beagle Dog Plasma Concentrations of Milrinone Following A Single 5 mg/kg PO Administration As Immediate Release Tablets In A Gelatin Capsule

| | Dog #1 | | Dog #2 | | Dog #3 |
|---|---|---|---|---|---|
| Animal Weight (kg) | 5.571 | Animal Weight (kg) | 9.257 | Animal Weight (kg) | 9.653 |
| Dose (mg) | 28 | Dose (mg) | 46 | Dose (mg) | 48 |
| Actual Dosage (mg/kg) | 5.03 | Actual Dosage (mg/kg) | 4.97 | Actual Dosage (mg/kg) | 4.97 |

| Time (hr) | Sample Conc. (ng/mL) | Sample Conc. (ng/mL) | Sample Conc. (ng/mL) | Mean Conc. (ng/mL) | SD (ng/mL) |
|---|---|---|---|---|---|
| 0 | BLQ | BLQ | BLQ | BLQ | N/A |
| 0.5 | 1840 | 2440 | 3570 | 2617 | 878 |
| 1 | 1750 | 2590 | 3680 | 2673 | 968 |
| 1.5 | 1210 | 4020 | 2420 | 2550 | 1410 |
| 3 | 717 | 1990 | 737 | 1148 | 729 |
| 6 | 142 | 574 | 331 | 349 | 217 |
| 9 | 234 | 217 | 71.0 | 174 | 89.6 |
| 11 | 110 | 71.3 | 118 | 99.8 | 25.0 |
| 12 | 73.0 | 87.8 | 81.2 | 80.7 | 7.41 |
| 14 | 51.3 | 89 | 58.2 | 66.2 | 20.1 |
| 18 | 30.6 | 31.5 | 30.5 | 30.9 | 0.551 |
| 24 | 5.45 | 16.3 | 8.46 | 10.1 | 5.60 |
| 30 | 1.63 | 2.34 | 2.85 | 2.27 | 0.613 |
| 36 | 2.10 | 4.22 | 2.96 | 3.09 | 1.07 |
| 42 | 1.55 | 1.74 | 1.64 | 1.64 | 0.095 |
| 48 | 0.795 | 0.964 | 2.00 | 1.25 | 0.652 |

BLQ = Below Limit of Quantitation
N/A = Not Applicable

Example 7

TABLE 3

Individual Female Beagle Dog Plasma Concentrations of Milrinone Following A Single 5 Mg/Kg PO Administration as Extended Release Tablets In a Gelatin Capsule

| | Dog #4 | | Dog #5 | | Dog #6 |
|---|---|---|---|---|---|
| Animal Weight (kg) | 7.682 | Animal Weight (kg) | 9.083 | Animal Weight (kg) | 9.657 |
| Dose (mg) | 38 | Dose (mg) | 46 | Dose (mg) | 48 |
| Actual Dosage (mg/kg) | 4.95 | Actual Dosage (mg/kg) | 5.06 | Actual Dosage (mg/kg) | 4.97 |

| Time (hr) | Sample Conc. (ng/mL) | Sample Conc. (ng/mL) | Sample Conc. (ng/mL) | Mean Conc. (ng/mL) | SD (ng/mL) |
|---|---|---|---|---|---|
| 0 | BLQ | BLQ | BLQ | BLQ | N/A |
| 0.5 | BLQ | 1.19 | BLQ | BLQ | N/A |
| 1 | BLQ | 15.6 | 0.57 | 5.39 | 8.85 |
| 1.5 | 204 | 198 | 54.4 | 152 | 84.7 |
| 3 | 569 | 487 | 601 | 552 | 58.8 |
| 6 | 563 | 459 | 519 | 514 | 52.2 |
| 9 | 570 | 696 | 373 | 546 | 163 |
| 11 | 545 | 779 | 138 | 487 | 324 |
| 12 | 457 | 597 | 109 | 388 | 251 |
| 14 | 264 | 456 | 42.1 | 254 | 207 |
| 18 | 50.2 | 149 | 10.1 | 69.8 | 71.5 |
| 24 | 16.4 | 25.8 | 1.36 | 14.5 | 12.3 |

The above in vivo pharmacokinetic data shows plasma levels following administration of Milrinone at a dosage of 5 mg/kg. The plasma concentrations versus time profiles obtained after oral administration of immediate release (IR) Milrinone and extended release (ER) Milrinone (i.e. a composition of the present invention) were analysed. Table 1 shows pharmacokinetic data for the IR Milrinone and ER Milrinone formulation dosing. These data demonstrate that the ER Milrinone achieved a reduced Cmax in comparison to the IR Milrinone, and that the ER Milrinone maintained stable Milrinone plasma concentrations over a 12 hour period.

This in vivo data substantiates the in vitro release data obtained above in Example 6 and provides confirmation that the formulations of the present invention satisfy the requirements of the desired release profile.

Example 8

To exemplify the therapeutic utility of milrinone in patients with HFpEF the following study was performed. Patients with HFpEF underwent an invasive assessment of central hemodynamics by Swan Ganz catheterization under resting conditions and during symptom limited supine cycling. In particular, the pulmonary artery and pulmonary capillary wedge pressure were measured. It is well known that patients with HFpEF exhibit a rapid and excessive rise in pulmonary artery and pulmonary capillary wedge pressure due to left ventricular diastolic dysfunction. Following this measurement patients were randomly allocated to receive an intravenous bolus of milrinone 50μ/kg over 10 minutes or an infusion of saline. At the end of this infusion the measurements were repeated.

The results are shown in the table below:

| | Rest | | Exercise | |
|---|---|---|---|---|
| | Pulm. Art. Press mm Hg | Wedge Press. Mm Hg | Pulm. Art. Press mm Hg | Wedge Press. Mm Hg |
| Baseline (n = 4) | 21 ± 3 | 12 ± 2 | 41 ± 2 | 30 ± 2 |
| Placebo | 20 ± 1 | 12 ± 1 | 37 ± 1 | 25 ± 1 |
| Baseline (n = 4) | 21 ± 3 | 11 ± 1 | 49 ± 3 | 33 ± 1 |
| Milrinone | 15 ± 2* | 4 ± 1* | 32 ± 6* | 19 ± 2** |

**p < 0.01,
*p < 0.05

These data show that milrinone improves the hemodynamic response in patients with HFpEF during exercise and this effect would be expected to be beneficial in these patients.

The disclosure of every patent, patent application, and publication cite herein is hereby incorporated by reference in its entirety.

The citation of any reference herein should not be construed as an admission that such reference is available as "Prior Art" to the instant application.

Throughout the specification the aim has been to describe the preferred embodiments of the invention without limiting the invention to any one embodiment or specific collection of features. Those of skill in the art will therefore appreciate that, in light of the instant disclosure, various modifications and changes can be made in the particular embodiments exemplified without departing from the scope of the present invention. All such modifications and changes are intended to be included within the scope of the appended claims.

BIBLIOGRAPHY

1. Edelmann F., et al., Effect of Spironolactone on Diastolic Function and Exercise Capacity in Patients with Heart Failure with Preserved Ejection Fraction; JAMA, 2013, 309(8):781-791.
2. Komajda M. and Lam C. S. P., Heart Failure with Preserved Ejection Fraction: a Clinical Dilemma; European Heart Journal, 2014, 35:1022-1032.
3. Loffredo F. S., et al., Heart Failure with Preserved Ejection Fraction, Molecular Pathways of the Aging Myocardium; Circulation Research, 2014, 115:97-107.
4. Redfield M. M., et al., Effect of Phosphodiesterase-5 Inhibition on Exercise Capacity and Clinical Status in Heart Failure with Preserved Ejection Fraction; JAMA, 2013, 309(12): 1268-1277.
5. Sharma K. and Kass D. A., Heart Failure with Preserved Ejection Fraction, Mechanisms, Clinical Features, and Therapies; Circulation Research, 2014, 115:79-96.
6. Yancy C. W. et al., 2013 ACCF/AHA Guideline for the Management of Heart Failure, A Report of the American College of Cardiology Foundation/American Heart Association Task Force on Practice Guidelines, Circulation, 2013, 128:e240-e327.

What is claimed is:

1. A method of treating a patient having heart failure with preserved ejection fraction (HFpEF) comprising administering to the patient milrinone, or a pharmaceutically acceptable salt thereof;
   wherein the formulation permits delivery of milrinone in an amount to achieve steady state plasma levels effective to alleviate the symptoms of HFpEF;
   wherein delivery of milrinone is in the range of between 0.1 μg/kg body weight per minute to 20 μg/kg body weight per minute; and
   wherein the patient shows an abnormal measured exercise pulmonary artery pressure or an abnormal measured exercise pulmonary capillary wedge pressure.

2. The method of claim 1, wherein the patient shows an abnormal measured exercise pulmonary artery pressure.

3. The method of claim 2, wherein the patient shows an abnormal measured exercise pulmonary artery pressure of about 41 mmHg to about 49 mmHg.

4. The method of claim 1, wherein the patient shows an abnormal measured exercise pulmonary capillary wedge pressure.

5. The method of claim 4, wherein the patient shows an abnormal measured exercise pulmonary capillary wedge pressure of about 30 mmHg to about 33 mmHg.

6. The method of claim 1, wherein the patient shows a normal measured resting pulmonary artery pressure or a normal measured resting pulmonary capillary wedge pressure.

7. The method of claim 1, wherein after the administration of milrinone a measured pulmonary artery pressure or a measured pulmonary capillary wedge pressure of the patient is reduced.

8. The method of claim 7, wherein the measured pulmonary artery pressure is a resting pulmonary artery pressure.

9. The method of claim 8, wherein the resting pulmonary artery pressure is reduced about 29%.

10. The method of claim 7, wherein the measured pulmonary artery pressure is an exercise pulmonary artery pressure.

11. The method of claim 10, wherein the exercise pulmonary artery pressure is reduced about 35%.

12. The method of claim 7, wherein the measured pulmonary capillary wedge pressure is a resting pulmonary capillary wedge pressure.

13. The method of claim 12, wherein the resting pulmonary capillary wedge pressure is reduced about 64%.

14. The method of claim 7, wherein the measured pulmonary capillary wedge pressure is an exercise pulmonary capillary wedge pressure.

15. The method of claim 14, wherein the exercise pulmonary capillary wedge pressure is reduced about 42%.

16. The method of claim 1, wherein the patient shows symptoms of left ventricular diastolic dysfunction.

17. The method of claim 1, wherein the patient does not show symptoms of renal disease or cardiovascular disease.

18. The method of claim 17, wherein the patient does not show symptoms of renal disease.

19. The method of claim 17, wherein the patient does not show symptoms of cardiovascular disease.

20. The method according to claim 1, wherein the administration achieves a plasma concentration of milrinone in the range of 100 to 400 ng/mL.

21. The method of claim 1, wherein the patient has not been diagnosed with renal disease or cardiovascular disease.

22. The method of claim 21, wherein the patient has not been diagnosed with renal disease.

23. The method of claim 21, wherein the patient has not been diagnosed with cardiovascular disease.

24. A method of treating a patient having heart failure with preserved ejection fraction (HFpEF) comprising administering to the patient milrinone, or a pharmaceutically acceptable salt thereof;
   wherein the formulation permits delivery of milrinone in an amount to achieve steady state plasma levels effective to alleviate the symptoms of HFpEF;
   wherein delivery of milrinone is in the range of between 0.1 μg/kg body weight per minute to 20 μg/kg body weight per minute;
   wherein the patient shows an abnormal measured exercise pulmonary artery pressure of about 41 mmHg to about 49 mmHg or an abnormal measured exercise pulmonary capillary wedge pressure of about 30 mmHg to about 33 mmHg; and
   wherein the patient shows a normal measured resting pulmonary artery pressure or a normal measured resting pulmonary capillary wedge pressure.

* * * * *

UNITED STATES PATENT AND TRADEMARK OFFICE
CERTIFICATE OF CORRECTION

PATENT NO. : 11,291,660 B2
APPLICATION NO. : 16/700237
DATED : April 5, 2022
INVENTOR(S) : David Kaye It is certified that error appears in the above-identified patent and that said Letters Patent is hereby corrected as shown below:

In the Specification

Column 1, Line 36, delete "that that" and insert -- that --.

Column 1, Line 65, delete "F F" and insert -- HF --.

Column 2, Line 44, delete "FlFrEF." and insert -- HFrEF. --.

Column 2, Line 45, delete "FlFpEF" and insert -- HFpEF. --.

Column 2, Line 53, delete "FlFpEF" and insert -- HFpEF. --.

Column 2, Line 56, delete "FlFpEF" and insert -- HFpEF. --.

Column 3, Line 28 (Approx.), delete "-Ci-Cealkyl;" and insert -- -Ci-$C_6$alkyl; --.

Column 3, Line 29 (Approx.), delete "R" and insert -- -$R_3$ --.

Column 3, Line 30, delete "-N(Ci.C 6alkyl" and insert -- --N(Ci.$C_6$alkyl --.

Column 3, Line 31, delete "-$CO_2$Ci-C alkyl" and insert -- -$CO_2$Ci-$C_6$alkyl --.

Column 3, Line 37, delete "FlFpEF;" and insert -- HFpEF; --.

Column 3, Line 58, delete "-$CO_2$Ci-C alkyl" and insert -- -$CO_2$Ci-$C_6$alkyl --.

Column 4, Line 17 (Approx.), delete "-Ci-Cealkyl;" and insert -- -Ci-$C_6$alkyl; --.

Column 4, Line 36, delete "o" and insert -- of a --.

Signed and Sealed this
Nineteenth Day of July, 2022

Katherine Kelly Vidal
*Director of the United States Patent and Trademark Office*

CERTIFICATE OF CORRECTION (continued)
U.S. Pat. No. 11,291,660 B2

Column 4, Line 49 (Approx.), delete "-Ci-Cealkyl;" and insert -- -Ci-C$_6$alkyl; --.

Column 6, Line 15 (Approx.), delete "FIFpEF." and insert -- HFpEF. --.

Column 6, Line 17 (Approx.), delete "(FIFrEF)" and insert -- (HFrEF) --.

Column 7, Line 23, delete "FIFpEF;" and insert -- HFpEF; --.

Column 9, Line 19, delete "and or" and insert -- and/or --.

Column 9, Line 25, delete "(TR)" and insert -- (IR) --.

Column 10, Line 59, delete "polyglucolides" and insert -- polyglycolides --.

Column 10, Line 60, delete "polyglucolide" and insert -- polyglycolide --.

Column 17, Line 15, delete "10%>," and insert -- 10%, --.

Column 17, Line 65, delete "poly(methacylic" and insert -- poly(methacrylic --.

Column 18, Line 29, delete "et a/(Eds)," and insert -- et al(Eds), --.

Column 34, Line 46, delete "Milrinone" and insert -- Milrinone. --.

Column 35, Line 64, delete "sees," and insert -- secs, --.